(12) United States Patent
Cunningham et al.

(10) Patent No.: US 10,085,686 B2
(45) Date of Patent: Oct. 2, 2018

(54) TONGUE EVALUATION SYSTEM AND METHOD

(71) Applicant: NFANT Labs, LLC, Atlanta, GA (US)

(72) Inventors: Thomas J. Cunningham, Smyrna, GA (US); Louis F. Malice, Jr., Marietta, GA (US); Gilson J. Capilouto, Lexington, KY (US)

(73) Assignee: NFANT Labs, LLC, Atlanta, GA (US)

( * ) Notice: Subject to any disclaimer, the term of this patent is extended or adjusted under 35 U.S.C. 154(b) by 0 days.

(21) Appl. No.: 15/601,066

(22) Filed: May 22, 2017

(65) Prior Publication Data

US 2017/0251971 A1   Sep. 7, 2017

Related U.S. Application Data

(60) Division of application No. 14/665,644, filed on Mar. 23, 2015, now Pat. No. 9,687,192, which is a continuation-in-part of application No. 14/166,281, filed on Jan. 28, 2014, now Pat. No. 8,986,229, which is a division of application No. 13/479,640, filed on May 24, 2012, now Pat. No. 8,663,131.

(60) Provisional application No. 61/578,004, filed on Dec. 20, 2011, provisional application No. 61/490,892, filed on May 27, 2011.

(51) Int. Cl.
| | |
|---|---|
| *A61B 5/103* | (2006.01) |
| *A61B 5/00* | (2006.01) |
| *A61B 5/03* | (2006.01) |
| *A61B 5/22* | (2006.01) |
| *A61J 11/00* | (2006.01) |

(52) U.S. Cl.
CPC ............ *A61B 5/4552* (2013.01); *A61B 5/038* (2013.01); *A61B 5/228* (2013.01); *A61B 5/682* (2013.01); *A61B 2503/04* (2013.01); *A61B 2560/0462* (2013.01); *A61B 2562/0247* (2013.01); *A61B 2562/0261* (2013.01); *A61B 2562/168* (2013.01); *A61J 11/00* (2013.01)

(58) Field of Classification Search
CPC ...... A61B 5/228; A61B 5/4547; A61C 19/045
USPC ........................................................ 600/590
See application file for complete search history.

(56) References Cited

U.S. PATENT DOCUMENTS

| | | | | |
|---|---|---|---|---|
| 4,094,314 A | * | 6/1978 | Le Cornec ............. | A62B 9/022 128/204.26 |
| 4,509,913 A | * | 4/1985 | Lorenz .................... | F23N 1/027 236/15 BD |

(Continued)

*Primary Examiner* — Daniel Cerioni
(74) *Attorney, Agent, or Firm* — Quinn IP Law

(57) ABSTRACT

An apparatus for evaluating the tongue strength and coordination of a subject includes an intermediate device such as a lever which is pivotably attached to a coupling device and extends into a cavity of a nipple element. The lever is detached from the nipple and pivotable in response to deformation of the nipple element by a tongue force exerted on the nipple element by a subject during a suck-swallow-breathe sequence. The coupling device includes a sensing device to wirelessly transmit sensor outputs to a mobile device paired to the sensing device. The sensing device includes at least one sealed chamber defined by a membrane and a sensor. In one example, a first membrane and sensor senses pressure change in a fluid in the apparatus, and a second membrane and sensor is actuated by the intermediate device to sense deformation of the nipple element. A method using the apparatus is provided.

18 Claims, 10 Drawing Sheets

(56) References Cited

U.S. PATENT DOCUMENTS

| | | | | |
|---|---|---|---|---|
| 4,697,601 | A | * | 10/1987 | Durkee ................. A61B 5/228 600/590 |
| 2006/0079814 | A1 | * | 4/2006 | Barlow ................. A61B 5/038 600/590 |
| 2008/0183107 | A1 | * | 7/2008 | Miller ................... A61B 5/228 600/590 |
| 2009/0156967 | A1 | * | 6/2009 | Cohen ................. A61B 5/1107 600/590 |
| 2012/0143091 | A1 | * | 6/2012 | Annett ................. A61B 5/228 600/590 |
| 2015/0196247 | A1 | * | 7/2015 | Lau ....................... G06F 19/34 600/301 |

* cited by examiner

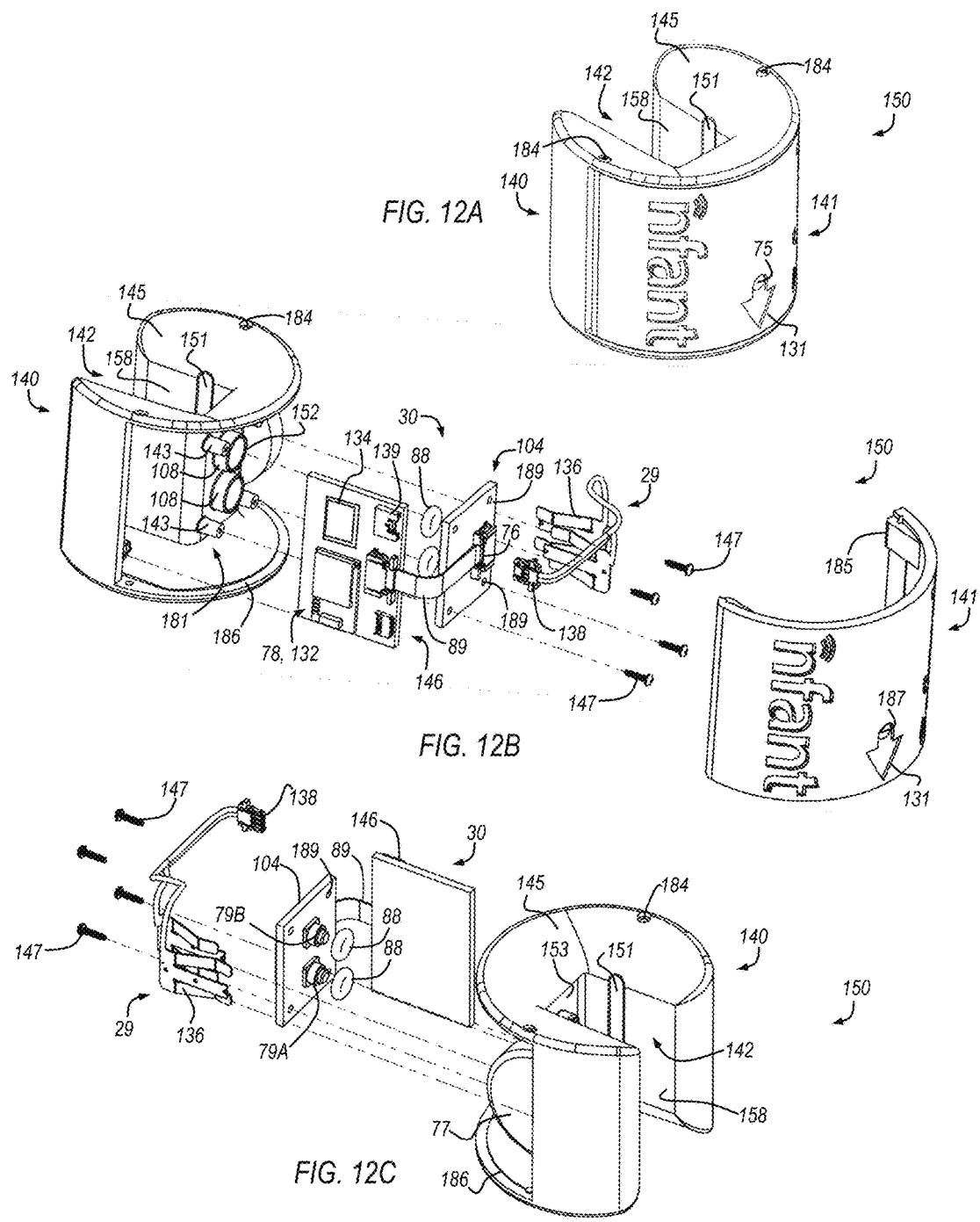

TONGUE EVALUATION SYSTEM AND METHOD

CROSS-REFERENCE TO RELATED APPLICATIONS

This application claims the benefit of U.S. non-provisional application Ser. No. 14/665,644 filed Mar. 23, 2015, U.S. non-provisional application Ser. No. 14/166,281 filed Jan. 28, 2014 and issued as U.S. Pat. No. 8,986,229 on Mar. 24, 2015, U.S. non-provisional application Ser. No. 13/479,640 filed May 24, 2012 and issued as U.S. Pat. No. 8,663,131 on Mar. 4, 2014, U.S. provisional application 61/490,892 filed May 27, 2011, and U.S. provisional application 61/578,004 filed Dec. 20, 2011, which are each hereby incorporated by reference in their entirety. U.S. non-provisional application Ser. No. 14/665,644 is a continuation-in-part of U.S. non-provisional application Ser. No. 14/166,281 which is a divisional application of U.S. non-provisional application Ser. No. 13/479,640 which is a non-provisional application of U.S. provisional application 61/490,892 and U.S. provisional application 61/578,004.

TECHNICAL FIELD

The present disclosure relates to the field of biomechanics and more specifically to the evaluation of tongue movement, strength and coordination.

BACKGROUND

Measuring the movement, strength and coordination of an infant tongue during sucking on the nipple of a bottle or pacifier presents several challenges including, for example, the limited oral space of the infant available for direct measurement and alteration of motor control feedback mechanisms induced at the tongue interface, the limited amount of space available for instrumentation of the nipple, alterations required for instrumentation of the nipple which could affect natural feeding patterns, and obtaining accurate and precise measurements of tongue contact with the nipple interface. There are two stages of feeding where the tongue is applied to the nipple. During one stage, compression (squeezing) of the nipple by forces exerted on the nipple by the tongue compresses the nipple against the palate. In a nutritive sucking condition, a volume of fluid present in the nipple is pushed out of the nipple and into the oral cavity due to compression of the nipple. In the other stage, with the oral cavity sealed, the jaw and tongue drop down and away from the palate, enlarging the oral cavity and creating negative intra-oral suction. In a nutritive sucking condition, fluid is drawn (sucked) out of the nipple. Both stages are essential to infant feeding.

Adaptations to tongue muscle including decline of or lack of improvement in tongue strength and coordination may occur in premature infants who are artificially fed for a period of time. Using animal models, researchers have documented significant negative changes in tongue muscle responsiveness as a result of artificial feeding of newborn rats, which result in long term difficulties with feeding. As many as forty to seventy percent of premature infants exhibit both immature and atypical feeding patterns and those requiring prolonged respiratory support and those experiencing delayed oral feeding are most often affected. Because artificial feeding of premature infants may not be avoidable, determining whether tongue force is adequate for safe, efficient oral feeding, and developing interventions that lessen or eliminate any negative impact on the tongue muscle, such as interventions for strengthening the tongue during non-nutritive suck (NNS) and nutritive suck (NS), are necessary. Clinical use of NNS with preterm infants to promote oral feeding is well documented. Indications are that NNS intervention has a positive impact on transition from tube feedings to oral feedings, improves bottle feeding performance and decreases length of stay. Volume intake, number of tube feedings prior to reaching full oral feeds, and impact on growth and weight gain are outcomes that have not been positively associated with NNS, and the impact of NNS on other important oral feeding outcomes is not clear. Current measurement and evaluation methods are subjective in nature and provide limited empirical evidence relative to assessment of infant feeding and swallowing.

SUMMARY

A system, method and apparatus to noninvasively evaluate movement, strength and coordination of the tongue of a subject is provided. The apparatus for evaluating the movement, strength and coordination of the tongue of a subject includes a coupling device including a coupling element. The coupling element includes a wall defining a passage. The wall defines a passage opening in communication with the passage and further defines an aperture in communication with the passage. The coupling element includes a coupling end configured to receive a nipple element such that the passage is in fluid communication via the passage opening with a nipple cavity defined by the nipple element. A sensor plug of the device encloses and seals the aperture. The coupling element includes a receiver disposed in the passage. The device further includes a lever defining a lever end. The lever is pivotably attached to the receiver at a pivot point such that the lever end extends out of the passage via the passage opening and extends into the nipple cavity and such that the lever end is detached from and in contact with a nipple surface defining the nipple cavity. Deflection of the lever end causes an actuator defined by the lever to actuate movement of the sensor plug. The lever end is deflectable by deformation of the nipple element such that the movement of the sensor plug corresponds to the deformation of the nipple. Deformation of the nipple element exerts a deformation force via the nipple element to deflect the lever end. The actuator is in contact with the sensor plug such that the sensor plug exerts a resistive force via the lever end. Movement of a tongue of a subject, for example, during a suck-swallow-breathe cycle of a feeding session, exerts a tongue force on the nipple element such that deformation of the nipple element occurs by movement of the tongue of the subject, and such that movement of the sensor plug corresponds to at least one of the movement of the tongue and the tongue force.

Measurements of tongue movement and/or the tongue force can be used to determine tongue strength and tongue coordination parameters of an infant subject, including tongue force applied to a nipple during non-nutritive suck (NNS) and nutritive suck (NS). An intervention method directed at increasing NS tongue strength and coordination as well as NNS tongue strength and coordination of a subject with the intended outcome of positively impacting transition from tube feedings to oral feedings by improving bottle feeding performance of the subject is provided. The system, method and apparatus are configured to obtain direct measurement of the force of the tongue on the nipple interface in a noninvasive manner and to evaluate kinetic changes to the nipple during NNS and NS measurement by measuring tongue movement. The magnitude and direction of forces applied by the tongue to the nipple can be calculated through a calibration process of the evaluation apparatus and kinematic analysis of the applied forces such that measurements of tongue strength, work, impulse, and power or other derivations of force and time may be calculated from movement measurements obtained using the evaluation apparatus described herein.

Movement measurements obtained using the apparatus may be used to calculate tongue force and derive tongue strength parameters and to evaluation tongue coordination. The evaluation apparatus includes an intermediate device, configured to be positioned within a nipple element and to provide an output in response to deformation of the nipple element by a deformation force exerted on the nipple element by the tongue of a subject during a sucking event. The output may be a resistive force exerted by the lever end of the intermediate device against the tongue of the subject during the sucking event, a movement measurement of the deformation force exerted on the nipple element during the sucking event, a pressure measurement corresponding to a change in fluid pressure of the fluid in the feeding apparatus, or a combination of these. The resistive force may be known or determined by calibration. The movement measurement output may be calibrated to the deformation or deformation force. The sucking event may be a nutritive sucking event wherein a fluid may be provided to the subject via the nipple element and the fluid may be in contact with the insert during the nutritive sucking event such that the nutritive sucking (NS) capability of the subject may be evaluated. The evaluation apparatus may be configured for non-nutritive sucking such that the non-nutritive sucking (NNS) capability of the subject may be evaluated.

The intermediate device in one example is configured as a lever including a lever end which is in contact with, but not attached to, the inner surface of a nipple element, such that the lever is pivotable relative to a pivot point established by pivotably attaching the lever to a coupling device sealably attached to the nipple element, by deformation of the nipple to provide an output which is a movement measurement of the deformation force exerted on the nipple element by a subject during the sucking event. The nipple element may have a known compliance to provide an output which is a resistive force exerted in opposition to the deformation force and/or against the tongue of the subject during the sucking event. A compliance element such as a sensor membrane in contact with the lever, e.g., in contact with the intermediate device, may output a resistive force exerted in opposition to the deformation force exerted by the tongue of the subject, such that the effective or total resistive force exerted against the subject's tongue during an evaluation session, e.g., during a suck-swallow-breathe cycle of the evaluation session, is defined by the combination of the compliance of the nipple element and the compliance of the compliance element, e.g., the sensor membrane exerting a membrane force on the intermediate device, e.g., on the lever.

The evaluation apparatus includes a coupling device configured to be operatively connected to a nipple element, to position the insert relative to the nipple element and/or receive the movement measurement output provided by the insert. The coupling device includes a housing assembly which contains a sensing device. The housing assembly may also be referred to as an SSB sensing device, where SSB as that term is used herein refers to the suck-swallow-breathe cycle performed by a subject on a nipple, which may be a NS nipple or a NNS nipple such as a pacifier. The housing assembly is uniquely identified to an individual subject and is configured for reuse with that individual subject, such that data transmitted by that housing assembly can be identified to that individual subject and stored and analyzed to develop a data history for that individual subject. The coupling device includes a coupling assembly, which in the example described herein is a single use assembly, e.g., is non-usable such that a new coupling assembly is required for each feeding session conducted with an individual subject. The coupling assembly is removably attached to the housing assembly, and is configured to be sealably attached to a nipple element at a first end and to a container at a second end to provide a sealed apparatus chamber partially defined by a passage of the coupling assembly, to contain fluid in fluid communication with the nipple element. The intermediate device is positioned within the passage of the coupling assembly and pivotably attached therein such that the intermediate device, e.g., the lever, is in contact with the liquid in the passage during the sucking event.

In one example, the coupling device includes a wall defining a passage and an aperture in communication with the passage. A sensor plug is operatively attached to the wall to enclose and seal the aperture. A receiver is disposed in the passage, and an intermediate device configured as a lever is pivotably attached to the receiver at a pivot point. The lever defines a lever end, and a tail end. The pivot point is intermediate the lever end and the tail end. Deflection of the lever end causes an actuator defined by the lever to actuate movement of the sensor plug. The actuator is in contact with the sensor plug. The sensor plug is intermediate a sensor and the passage, where the sensor is configured to sense movement of the sensor plug and to generate a sensor output corresponding to the movement of the sensor plug by the actuator, where the sensor output is correlated to the deflection of the lever end.

In another example, the coupling device includes a wall defining a passage and an aperture in communication with the passage. A sensor plug is operatively attached to the wall to enclose and seal the aperture and defines a membrane. The membrane is movable such that a change in a fluid pressure of a fluid in the passage actuates a movement of the membrane corresponding to the change in the fluid pressure. The membrane is intermediate a sensor and the passage, where the sensor is configured to sense movement of the membrane and to generate a sensor output corresponding to the movement of the membrane, where the sensor output is correlated to the fluid pressure of the fluid in the passage.

A system for evaluating the strength of the tongue of a subject during a sucking event is provided. The system includes the evaluation apparatus in secured and preferably wireless communication with a mobile device hosting an evaluation application. The mobile device is in communication with a web portal configured to administer the evaluation system, including administering security protocols, storing data received from the evaluation apparatus via the mobile device, associating the data with a subject and providing data analysis and history for each subject paired with a housing assembly, e.g., paired with a sensing device of an evaluation apparatus. A method for evaluating the strength of the tongue of a subject using the evaluation system is also provided.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 12A is a schematic perspective view of the housing assembly of FIGS. 4 and 5;

FIG. 12B is a schematic exploded view of the housing assembly of FIG. 12A including a housing, a sensor assembly and a housing cover;

FIG. 12C is another schematic exploded view of the housing assembly of FIG. 12A;

DETAILED DESCRIPTION

Figure 1:
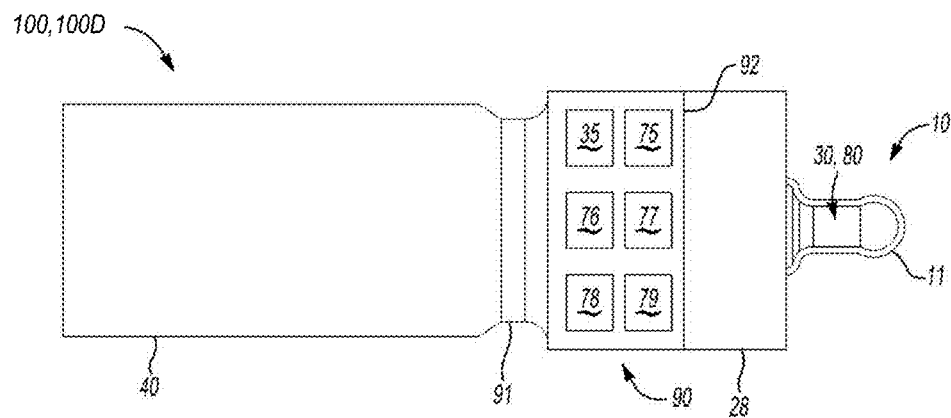
FIG. 1 is a schematic side view of a tongue evaluation apparatus including a coupling device.

A system, method and apparatus for noninvasive evaluation of tongue movement, tongue strength and/or tongue coordination, for example, infant tongue movement, strength and coordination during nutritive suck (NS) and non-nutritive suck (NNS), are provided. The system and method may include an intervention directed at training the tongue movement and increasing NS tongue strength and coordination and/or NNS tongue strength and coordination of a subject with the intended outcome of positively impacting a transition from tube feedings to oral feedings by improving bottle feeding performance of the subject. The system, method and apparatus are configured to enable noninvasive direct measurement of the force of the tongue on the nipple interface and kinematic changes to the nipple during non-nutritive suck and nutritive suck and movement measurement. Broadly, the system, method and apparatus comprise providing deformable materials which may be associated with sensors, allowing measurement of the movement of the tongue and degree of deformation of the deformable materials, the amount of force induced, etc., such as during application of force by the tongue during sucking. Without intending any limitation, the deformable materials may be configured as or associated with a nipple shape of known configuration, such as an infant bottle nipple, a pacifier nipple, and the like. The sensor or sensors may be calibrated such that signals provided by the sensors over time may be collected and analyzed to identify stages of the feeding process and to determine the magnitude and direction of forces applied by the tongue of a subject to the nipple and kinematic analysis of the applied forces may be performed to derive the power, impulse, and work performed by the tongue, and other measurements of tongue strength which may be derived from the sensor signals.

As used herein, "nutritive suck" refers to the process of a subject ("subject") feeding with a bottle or breast and receiving fluid. Therefore, a "nutritive suck" ("NS") condition is one where the nipple element and/or the apparatus including the instrumented nipple is configured such that liquid is passed through the nipple to the subject, during a sucking event. For example, the NS nipple may define a nipple aperture through which liquid in communication with the nipple aperture, which may be liquid in a bottle or other container to which the NS nipple is fluidly attached, flows through the nipple into a subject's oral cavity during a sucking or feeding event. In nutritive suck the fluid is typically a substance ingested by the infant during feeding, such as infant formula, water, milk, etc. As used herein, fluid type is not meant to be limiting.

As used herein, "non-nutritive suck" refers to the process of a subject performing the same task as nutritive feeding but not receiving fluid. A "non-nutritive suck" ("NNS") condition is one where liquid is not flowed through the nipple, e.g., no feeding occurs. The nipple in NNS may contain a nipple aperture for passage of fluid or may be sealed. In a non-limiting example, a NNS nipple may be configured without a nipple aperture such that fluid flow through the nipple is prevented. In another example, a NNS nipple may be configured as a pacifier. In another example, an evaluation apparatus may include a nipple with a nipple aperture which may be used in either of a NS (liquid provided) condition or NNS (no liquid provided) condition.

As used herein, an "instrumented nipple" is a nipple element including, attached to or in selective communication with an insert, where the insert may include one or more of a compliance element, a sensor, and an intermediate device. As used herein, "compliance" is a nipple or nipple element's tendency to resist deformation caused by applied forces, for example, the forces applied by the subject's tongue against the nipple during sucking, and a "compliance element" is an insert configured to modify the compliance of an instrumented nipple including the compliance element relative to a nipple element which is not instrumented. As used herein, "tongue strength" refers to a singular measure or plurality of measures used to assess the ability of the tongue to perform its function. Tongue strength measures include but are not limited to force, impulse, power and work. As used herein, "tongue coordination" refers to single measure or plurality of measures uses to assess the temporal functions of neuromuscular control or strength measures including but not limited to frequency, variation or timing of sucking events.

Figure 2:
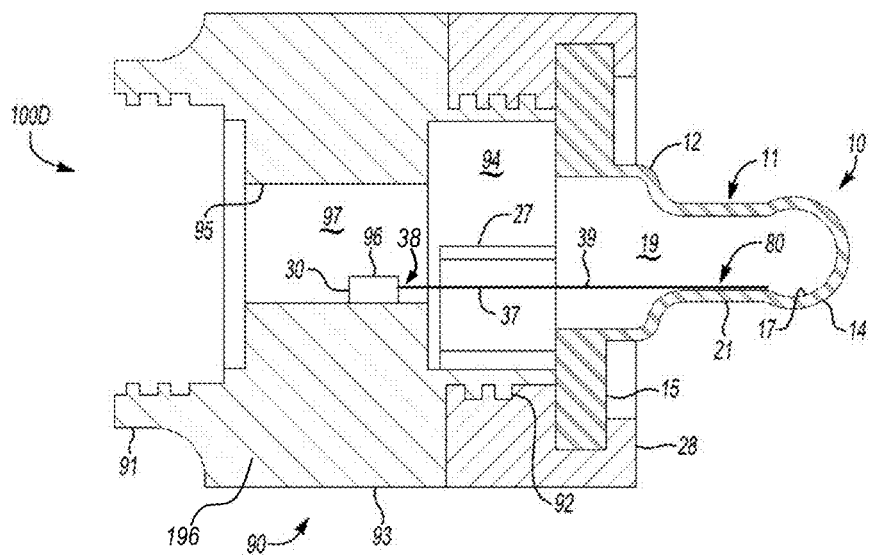
FIG. 2 is a schematic cross-sectional view of the tongue evaluation apparatus of FIG. 1 including the coupling device.

Referring to the drawings wherein like reference numbers represent like components throughout the several figures, the elements shown in FIGS. 1-17 are not to scale or proportion. Accordingly, the particular dimensions and applications provided in the drawings presented herein are not to be considered limiting. FIGS. 1-2 show a schematic illustration of an example configuration of a tongue evaluation apparatus 100 indicated generally at 100D and including a coupling device 90 and an instrumented nipple 10. FIGS. 4-13E show another example configuration of a tongue evaluation apparatus 100 indicated generally at 100E and including a coupling device 90 and instrumented nipple 10. The tongue evaluation apparatus 100 may be referred to herein as an evaluation apparatus 100. As used herein, a "subject" is the subject whose tongue movement and/or tongue strength and coordination is being evaluated by the evaluation apparatus 100. The subject may be an infant, non-infant child, or adult subject who participates as the subject of an evaluation session, also referred to herein as a feeding session, where the subject receives the nipple element 11 into the subject's oral cavity and it is the subject's tongue which exerts a deformation force on the nipple element during the evaluation session. As used herein, a "user" is a person using the evaluation apparatus 100 to evaluate the tongue movement and/or tongue strength and coordination of the subject, and who may, for example, perform one or more activities with the evaluation apparatus 100 such as assembly, set-up, calibration, and operation of the apparatus 100, including instructing the subject and/or, for example, with an infant subject, conducting the evaluation session by feeding the subject using the evaluation apparatus 100. A user may be, by way of non-limiting example, a clinician, a medical practitioner, a feeding therapist, a parent, a caregiver, etc. The user may be an individual sufficiently trained in the operation of the evaluation apparatus 100 to establish a communication link between the evaluation apparatus 100 and a mobile device 159 and conduct an evaluation feeding session, such that data collected during the feeding session can be transmitted via the mobile device 159 to a clinician, etc. for remote evaluation of the condition of the subject.

Figure 3:
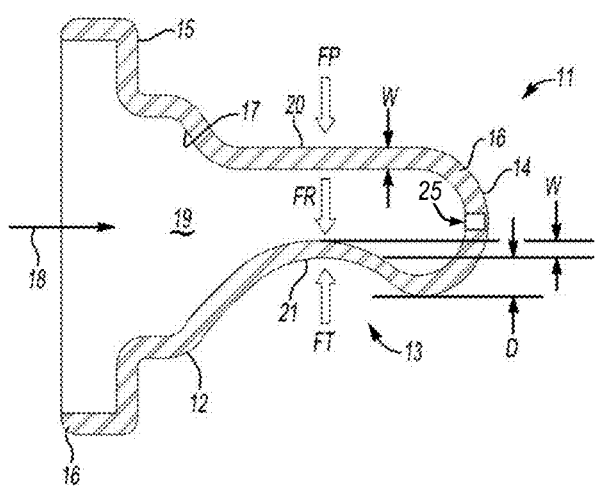
FIG. 3 is a schematic cross-sectional view of a nipple element shown in a sucking condition.

The instrumented nipple 10 includes a nipple element 11 and an intermediate device 37 disposed in a nipple cavity 19 defined by the nipple 11. Referring to FIG. 3, shown is a schematic cross-sectional view of the nipple element generally indicated at 11. The nipple element 11 is shown in a sucking condition, e.g., in a deformed condition caused by a deformation force exerted on the nipple 11. The deformation force may be a tongue force FT exerted by a subject on the nipple element 11 during sucking or during a feeding session conducted with the subject using the evaluation apparatus 100, or a calibration force FC exerted during a calibration process to calibrate the evaluation apparatus 100, as described herein. The nipple element 11 is formed of a deformable material such as silicone, rubber, or other polymeric or natural material.

The nipple element 11 may be a standard nipple, e.g., a nipple configured as a pacifier or feeding nipple, also known as a bottle nipple, which is available over the counter. In a non-limiting example, the nipple element 11 may be configured for use with an infant. The nipple element 11 may be configured as a non-infant (non-infant child or adult) pacifier and may be instrumented to provide an instrumented nipple 10 for use in evaluating the tongue movement, tongue strength, tongue coordination, and/or swallowing capabilities of a non-infant subject, for example, an elderly subject. In this example, the non-child nipple element 11 may be configured for either NS or NNS and adaptable to a fluid source or as otherwise described herein to enable evaluation of the subject's swallowing capability. It would be understood based on these examples that the configuration of the nipple 11 element shown in the figures is not intended to be limiting, and the nipple element 11 may be of a standard (over the counter) configuration or a non-standard (customized) configuration. The nipple element 11 may be referred to herein as an unmodified nipple or as a non-instrumented nipple, in which case that the nipple element 11 refers to a standard nipple element, e.g., a nipple element, bottle nipple, etc. which has not been modified from its standard configuration or the nipple element 11 without instrumentation. A nipple element 11 may be combined with one or more inserts, as described in further detail herein, to provide an instrumented nipple 10.

In a typical configuration, the nipple element 11 includes a tip portion 14 at one end and a flange portion 15 at the opposing end. The tip portion 14 is adjacent the intermediate portion 13 of the nipple, also referred to herein as the nipple body 13. A base portion 12 is interposed between the body 13 and the flange portion 15. The nipple element 11 shown in FIG. 3 is configured as a nutritive suck (NS) nipple, such that the the nipple wall 16 defines a nipple cavity 19 which is open at the tip 14 via a nipple aperture 25, and is open at the opposing end via an opening 18 defined by the flange portion 15. In a non-limiting example, the nipple element 11 may be configured as a pacifier and may include, as shown in FIG. 2, an extension 27 provided as a handle for inserting, positioning and removing the nipple element 11 relative to a subject's oral cavity. In the example shown in FIG. 2, the extension 27 is received into the cavity 94 of the coupling device 90. The subject's oral cavity may also be referred to herein as the subject's mouth.

The nipple element 11 is shown FIG. 2 in a first condition, which may also be referred to herein as a resting or non-deformed condition. In the resting condition, minimal to no forces are exerted by the tongue on the nipple element 11 such that deformation of the nipple element 11 is minimal to none. A nipple element 11 is shown in FIG. 3 in a second condition, which may also be referred to herein as a sucking or deformed condition. In the sucking condition, the nipple is positioned in the subject's mouth such that a first portion 20 of the nipple element 11 is in contact with the subject's palate (not shown), and a constraining force FP is exerted by the palate against the first portion 20, which may be referred to herein as the palate facing portion of the nipple. During sucking, the subject's tongue (not shown) exerts a tongue force FT on a second portion 21 of the nipple element 11, as shown in FIG. 3. The second portion 21 may be referred to herein as the tongue facing portion 21 of the nipple element 11 and generally opposes the palate facing portion 20 when the nipple is positioned in the subject's mouth. In a sucking condition, as shown in FIG. 3, the tongue force FT compresses the nipple element 11 by deforming the nipple wall 16 of the tongue facing portion 21 toward the palate facing portion 20. The magnitude of the deformation in the sucking or deformed condition may be measured by a deformation distance D, as shown in FIG. 3. It would be understood that the deformation distance D of the nipple in the resting condition shown in FIG. 2 is zero.

Figure 14:
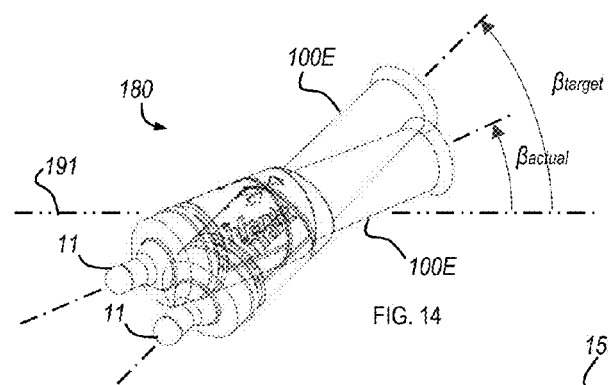
FIG. 14 is a schematic perspective view of the evaluation apparatus of FIG. 4 in a first tilted position and in a second tilted position.

The nipple element 11 exerts an effective resistive force FR in opposition to the tongue force FT. The effective resistive force FR is at least partially a function of the compliance of the nipple element 11, where the compliance of the nipple element 11, as that term is used herein, is the tendency of the nipple element 11 to resist deformation caused by applied forces such as the tongue force FT. The compliance of the nipple element 11 and the resistive force FR may be determined by one or more factors, including but not limited to the material characteristics of the nipple element 11, such as the material type, elasticity, hardness, etc. of the nipple element 11, and the wall thickness W of the nipple wall 16. The effective compliance of the nipple 10 (including the nipple element 11) and the effective resistive force FR exerted on the tongue of the subject may be modified by changing the configuration of the nipple wall 16 in the tongue facing portion 21 and/or adding a compliance element 80 configured to exert a resistive force in opposition to a tongue force FT, where in this instance, the effective resistive force FR is partially defined by the compliance of the nipple element 11 and partially defined by the resistive force exerted by the compliance element 80. Instrumented nipples 10 of varying compliance and resistive force FR may be used in an intervention method as shown in FIG. 14 to develop tongue strength and coordination in a user subject such as an infant, which may be a preterm infant.

Deformation forces exerted on a nipple in a sucking condition can be evaluated by instrumentation of the nipple element 11 using an insert including or configured as a sensing device, such as but not limited to a sensing device 30 described in further detail herein and illustrated by the figures, to provide an instrumented nipple 10. The compliance and/or resistive force of a nipple may be modified by instrumentation of the nipple element 11 using an insert including or configured as a compliance element 80 having a known compliance and resistive force FR, such as but not limited to a compliance element 80 to provide an instrumented nipple 10. The known compliance and/or resistive force FR may be determined by configuration of the instrumented nipple 10 or by calibration of the instrumented nipple 10 using a calibration apparatus as described in U.S. non-provisional application Ser. No. 13/479,640 filed May 24, 2012 and issued as U.S. Pat. No. 8,663,131, incorporated herein in its entirety. The term "instrumented nipple," as used herein, refers to a nipple element 11 including, in contact with, or in operative communication with at least one insert, where the insert comprises one or more of an intermediate device 37, a sensing device 30, a compliance element 80, with the insert configured to directly measure the deformation force exerted on the nipple element 11 and/or to provide an instrumented nipple 10 characterized by a known effective compliance or calibrated resistive force FR, where the effective compliance is at least partially defined by the compliance of the nipple element 11.

As shown in FIG. 2, the coupling device 90 includes a sensing device 30 configured to measure deformation of the nipple element 11. In one example the sensing device 90 includes an optical sensing device to measure the deformation of the nipple element 11. In another example, shown in FIG. 2, the coupling device includes an intermediate device 37 disposed in the nipple cavity 19 and in communication with the sensing device 30, such that the intermediate device 37 detects deformation of the nipple element 11 and actuates the sensing device 30 to sense or otherwise measure the deformation. In the example shown in FIG. 2, the intermediate device 37 is configured as a cantilever element affixed at a first end 38 to coupling device 90 via at least one of the receiver 96 and the sensing device 30, such that the cantilever element is in operative communication with the sensing device 30, and the free (non-affixed) end opposing the attached end 38 is positioned within the nipple cavity 19 adjacent the inner surface 17 of the nipple element 11 such that the free end of the cantilever is adjacent to but detached from the nipple element 11 and the free end of the cantilever is moveable in response to deformation of the nipple element. Deflection of the free end of the cantilever in response to movement of the nipple element resultant from the deformation force exerted on the nipple element 11 is transmitted via the cantilever element, e.g., via the intermediate device 37 defining the cantilever element, to the sensing device 30. The sensing device 30, in this example, may include a linear displacement sensor in communication with the cantilevered intermediate device 37 to sense the displacement (deformation change) of the cantilevered intermediate device 37 and provide an output in response to the displacement (deformation change).

The example shown in FIG. 2 of an intermediate device 37 defining a cantilever is non-limiting, and it would be understood that other configurations of an intermediate device 37 may be used to generate an output in response to movement of the nipple element resultant from a deformation force exerted on the nipple element, where the deformation force may include, as shown in FIG. 3, a tongue force FT exerted on the nipple element 11 by the tongue of a subject during a sucking event. By way of non-limiting example, the intermediate device 37 may include one or more of, and/or be configured as one or more of a triggering device, a connector, a mechanical pulley or cam system, a pivotable lever, a pivot, an electrical, pneumatic, magnetic, hydraulic or optical switch, a sensor, a cantilever, and/or an actuator, which is positioned in the coupling device 90 relative to the nipple element 11 to output a response to deformation of the nipple element 11. The output may be measurable as a force, displacement, magnetic property, pressure, optical characteristic, etc. as defined by the configuration of the intermediate device 37. In one example, the intermediate device 37 may include a piezoelectric material configured to sense deformation changes in a compliance element 80 position on or adjacent to the nipple element 11. The intermediate device may be in communication with the sensing device 30 and/or a data collector/analyzer, such that the intermediate device when actuated by the deformation change of the compliance element 80 transmits or transfers the deformation change to the sensing device 30 and/or to the data collector/analyzer, as an output, where the output may be in the form of an electrical, magnetic, sound, optical, or pneumatic signal, a displacing force, stress or strain provided as an input to the sensing device 30 or the data collector/analyzer. The data collector/analyzer may be included in a mobile device 159 in communication with the sensing device 30, as illustrated by the tongue evaluation system 105A shown in FIG. 15. In another example, shown in FIGS. 4-7, a sensing device 30 is in communication with an intermediate device 37, which is partially disposed in the nipple cavity 19 to provide an instrumented nipple 10, and which is pivotably mounted such that when the nipple element 11 is deformed, the intermediate device 37 pivots to cause an actuator 74 to actuate the sensing device 30, such that the sensing device 30 senses or otherwise measures deformation of the nipple element 11.

The tongue evaluation apparatus 100 may be calibrated such that the output provided by the intermediate device 37 in response to deformation of the nipple element 11 by a known deformation force FT may be determined. The intermediate device 37 may be configured to provide a resistive force FR which may be known based on characteristics of the intermediate device 37, including the configuration of the intermediate device 37, the method of attaching the intermediate device 37 to the coupling device 90, the inclusion of a compliance element 80 in the intermediate device 37 and/or acting on the intermediate device 37, the material, shape, dimensions, etc., of the intermediate device 37, and/or which may be determined by calibration. The response to the deformation force FT by the intermediate device 37 is transmitted as an output to the sensing device 30, thereby providing a means for direct measurement of the deformation force exerted on the nipple element 11 and/or the intermediate device 37, and/or evaluation of a subject's tongue movement, strength and/or coordination when the deformation force exerted on the nipple is the tongue force FT exerted on the nipple element 11 of the evaluation apparatus 100 by the subject. By way of non-limiting example, an apparatus and method for calibration of the evaluation apparatus is described in U.S. non-provisional application Ser. No. 13/479,640 filed May 24, 2012 and issued as U.S. Pat. No. 8,663,131, incorporated herein in its entirety. Forces applied by the tongue during evaluation of a subject correspond to the following equation:

$$FT \propto DT \cong FC \propto DC \propto \text{Nipple Compliance} \quad (1)$$

where FT are the forces produced by the tongue on an instrumented nipple 10, DT is the distance the nipple deforms due to the tongue, FC are the forces applied to the instrumented nipple 10 during a calibration procedure to deform the instrumented nipple 10, where the distance the nipple deforms due to the calibration force are DC. An example of a deformation distance D is shown in FIG. 3, which is illustrative of the distance DT the nipple element 11 is deformed by the tongue force FT of a subject when deformation is caused by the subject's tongue during a sucking event, and which is illustrative of the distance DC the nipple element 11 is deformed upon imposition of a calibration force FC. The sensing device 30 of the evaluation apparatus 100D, 100E may include pressure sensors 79A, 79B configured to detect changes in fluid pressure of fluid in the sealed apparatus chamber defined at least partially by a passage 97 of the coupling device 90, where the pressure in the sealed apparatus chamber is referred to herein as the fluid pressure. During calibration, changes in fluid pressure within the sealed apparatus chamber may be measured by the calibration apparatus (not shown) and used to calibrate the sensing device 30. It would be understood that calibration may not need to be performed for every nipple or at every instance of use of the evaluation apparatus 100, for example, after an initial calibration has been performed and/or when the properties of the various elements of the coupling device 90 and the nipple element 11 are established.

In the examples shown, the coupling device 90 includes a coupling element 93 which forms the body of the coupling device 90. The coupling element 93 is configured at a first end 91 to interface with a bottle 40 defining a bottle cavity 41 (see FIG. 5). The bottle 40 may be a standard infant feeding bottle (baby bottle), e.g., one which is available over the counter. In one example, the first end 91 may define a plurality of threads for engaging the threaded end 42 (see FIG. 5) of the bottle 40, to create a sealed interface between the bottle 40 and coupling device 90. The example provided herein is not limiting, and other configurations of the first end 91 may be used to create a sealed interface between a container or bottle 40 and the coupling device 90. For example, the first end 91 may be configured to snap on, clip to, or create an interference fit with the container 40 to provide a sealed interface. As shown in FIG. 6, a seal 116, which may be, for example, an O-ring or gasket, may be inserted between the bottle 40 and the coupling device 90 to provide a sealed interface between the bottle 40 and the coupling device 90. The seal 116 is made of an FDA Class V1 "food safe" (FS) material, which in the non-limiting example shown is a silicone or nitrile (synthetic rubber) FS material.

The coupling element 93 is configured at a second end 92 to interface with a collar 28. The collar 28 may be, in the example shown, a standard infant bottle collar or ring which is threadable onto the second end 92 of the coupling device 90 to retain the nipple element 11 in sealing contact with the coupling device 90. In one example, the second end 92 may define a plurality of threads for engaging the collar 28, where the plurality of threads may be configured substantially similar to the plurality of threads of a standard infant feeding bottle. The coupling device 90, thus configured, is readily attachable to a standard infant feeding bottle 40 and a standard bottle collar 28, where the term "standard" as used herein refers to an item which is readily available to a consumer in a standardized format. In the present example, a standard infant feeding bottle is one which is available over the counter, as that term is commonly understood. Likewise, a standard bottle collar is one which is available over the counter and is attachable to a standard infant feeding bottle, where it would be understood that the standard bottle collar and feeding bottle would have respective threaded interfaces which are compatible or corresponding to enable attachment of the collar 28 to the bottle end 92.

In the example shown in FIG. 2, first end 91 of the coupling device 90 defines a cavity 94 of sufficient depth to receive a nipple element 11 including an extension 27. In a non-limiting example, the nipple element 11 including the extension 27 may be configured as a standard, e.g., over the counter pacifier, such as a Soothie® pacifier, such that the evaluation apparatus 100D may be assembled using the coupling device 90, an insert which may be at least one of a sensing device 30 and a compliance element 80, and a standard bottle 40, a standard collar 28 and a nipple element 11, where the nipple element 11 may be a standard pacifier to provide an NNS configuration, or standard feeding nipple to provide an NS or NNS configuration. In an NS configuration, fluid may be flowed from a bottle 40 connected to the first end 91 of the coupling device 90 through a cavity 97 defined by an inner wall surface 95 of a wall 196 of the coupling element 93 and through a nipple aperture 25 of the nipple element 11. In the example shown, the cavity 97, which may also be referred to herein as a fluid passage 97, may be partially defined by the end cavity 94 defined by the second end 92 of the coupling element 93. The example provided herein is not limiting, and other configurations of the second end 92 may be used to position the nipple element 11 relative to the coupling device 90 and/or to retain the nipple element 11 in sealing contact with the coupling device 90. For example, the second end 92 may be configured with a recessed portion or groove into which the flange 15 of the nipple element 11 may be inserted or retained. The nipple element 11 may be configured to be extended over the second end 92 to create an interference fit with the coupling device 90 to provide a sealed interface without requiring the collar 28. The collar 28 may be configured to snap or clip onto the second end 92 or to otherwise be retained by the second end 92. Another example configuration is shown in FIGS. 4-7, and described in additional detail herein.

In an NNS configuration, the evaluation apparatus 100D may be used without a bottle 40. A plug (not shown) may be provided to enclose the first end 91 of the coupling device when used without a bottle 40, to protect the threaded interface, prevent contamination of or damage to the interior cavity 94 and/or to the fluid passage 97 of the coupling device 90, the receiver 96 or other components such as a sensing device 30, etc. housed therein. The plug (not shown) may be configured to sealably attach to the first end 91, to provide a sealed apparatus chamber defined by combination of the plug, the wall 196 of the coupling element 93, and the inner surface 17 of the nipple element 11.

As shown in FIGS. 1-2, the coupling device 90 may include a sensing device 30, an intermediate device 37, and/or a receiver 96 to receive and transmit data and/or sensor signals to, for example, a data collector/analyzer or a data storage device, which may be a portable data storage or memory device such as a SIM card, flash drive, etc. or other portable device in communication with the coupling device 90 which may include RAM or flash memory and be used to transfer the collected data to the data collector/analyzer. The communications interface 35 may be configured to transmit output signals from the sensing device 30 of the evaluation apparatus 100D, for example, by wirelessly transmitting the sensor signals to the data collector/analyzer using any suitable means of wireless transmission such as Bluetooth®, Bluetooth® Low-Energy (BLE), RFID, Wi-Fi, ZigBee®. In the example shown in FIG. 15, the coupling device 90 is in wireless communication via a communications interface 35 with a mobile user device 159 using Low-Energy Bluetooth®, which is also known as Bluetooth 4.0®, Smart Bluetooth®, and/or Bluetooth LE®. The mobile user device 159 in the example shown includes memory 178, an evaluation application 188, a processor 192, and a display 175 for receiving, analyzing and displaying the output signals received from the sensing device 30, as described in further detail herein. The evaluation application 188 and/or the processor 192 may be configured as a data collector/analyzer. The mobile user device 159, which may be referred to herein as the mobile device 159, may be configured as a laptop computer, notebook, a tablet, such as an iPad®, a smart phone, or the like.

The coupling device 90 may include a user interface 75, which may include a display and/or input/output interface for visually, audibly, or textually communicating data, analysis results, messages, instructions, alerts, etc. The coupling device 90 may include a transducer 76, which may be configured, for example, to convert an input signal received from a sensing device 30, intermediate device 37, pressure sensor 79, into an output signal to be provided to the communications interface 35, stored in a memory 78, displayed via the user interface 75, etc. The input signal may be an electrical, mechanical (force, stress, strain), electromagnetic, optical, chemical, pressure, or acoustic signal which may be converted by the transducer 76 into an output signal which may be, in a non-limiting example, an electrical, visual or audible signal. The coupling device 90 may include a power source 77, which may be a battery or power input interface, and memory 78 configured as one or more of Read Only Memory (ROM), Random Access Memory (RAM), electrically-erasable programmable read only memory (EEPROM), etc., of a size and speed sufficient for executing the functions performed by the coupling device 90.

The coupling device 90 may include the receiver 96 which may be configured to position, connect to, and/or receive one or more of the sensing device 30, the intermediate device 37 or a holder 39. The receiver 96, in one example, may be in operative communication with one or more of the communications interface 35, the user interface 75, the transducer 76, and the memory 78 and may be configured to transmit data and/or signals between the sensing device 30 and/or intermediate device 37 and one or more of these. The sensing device 30 may be integrated into the receiver 96 and/or coupling 90 as shown in FIG. 2, and output signals may be received via the intermediate device 37 in communication with the compliance element 80 and the integrated sensing device 30. In another example shown in FIGS. 4-7, the receiver 96 may be configured to receive the intermediate device 37 and to position the intermediate device 37 relative to the nipple element 11 and the sensing device 30. In the example shown, the intermediate device 37 is pivotable in the receiver 96 by deformation of the nipple 11, to actuate the sensor 79B in the sensing device 30.

The coupling device 90 may include one or more sensors 79 in communication with the cavity 94 and/or the fluid passage 97 defined by the coupling device 90. One or more of the sensors 79 may be configured as a pressure sensor. An apparatus chamber of the evaluation apparatus 100 may be formed by the bottle cavity 41, fluid passage 97 and nipple cavity 19, such that the pressure sensor 79 in communication with the sealed apparatus chamber thus formed by the connected nipple cavity 19 and fluid passage 97 can be used to measure pressure changes in the sealed apparatus chamber resultant from tongue movement of a subject, for example, during a sucking event, and the pressure measurements used in evaluating the tongue movement and/or tongue strength and coordination of the subject. Alternatively, the plug may be sealably attached to the first end 91 of the coupling device 90 to form a sealed apparatus chamber defined by the nipple cavity 19 and the fluid passage 97 to measure pressure changes in the sealed apparatus chamber thus formed, using the pressure sensor 79.

The tongue evaluation apparatus 100D including the coupling device 90 may be assembled in various configurations and with various combinations of sensing devices 30, compliance elements 80, intermediate devices 37, etc., including but not limited to the configurations shown in FIGS. 1-13E. Referring to FIG. 2, the evaluation apparatus 100D includes a nipple element 11 configured as a pacifier which is positioned in sealing contact with the second end 92 of the coupling element 93, and retained in position by the collar 28, to provide an NNS configuration. In an NNS configuration, a bottle 40 or a plug may be optionally attached to the first end 91 of the coupling element 93. Alternatively, a feeding nipple element 11 including a nipple aperture 25 (see FIG. 3) may be substituted for the pacifier nipple element to provide an NS configuration. In the NS configuration, a bottle 40 containing a fluid 24 may be attached as shown in FIG. 1. An intermediate device 37 including a compliance element generally indicated at 80 is positioned in the nipple cavity 19 to provide an instrumented nipple 10. The coupling device 90 includes an integrated sensing device 30 for receiving signals from the compliance element 80 via the intermediate device 37 which is in operative communication with the compliance element 80 and the integrated sensing device 30. In one example, the intermediate device 37 may be connected to the integrated sensing device 30 via the receiver 96.

The holder 39 may be provided to support or position the intermediate device 37 and/or the compliance element 80 with respect to the nipple element 11 and the receiver 96. The holder 39 may be integral to the intermediate device 37. The receiver 96 may be configured to receive the holder 39 in an oriented position relative to the nipple element 11, and/or tongue facing portion 21 of the nipple element 11. The receiver 96 may be integral to the coupling element 93. The compliance element 80 may be oriented or positioned to be deformed by and/or sense a deformation force exerted on the nipple element 11. The deformation force may be a tongue force FT exerted on the tongue facing portion 21 of the instrumented nipple 10 by a subject during a sucking event, such that noninvasive direct measurement of the deformation force FT may be made using the evaluation apparatus 100D to evaluate the tongue movement, tongue strength and coordination and/or sucking capability of the subject. In the example of the tongue evaluation apparatus 100E shown in FIGS. 4-10F, the holder 39 is integral to and defined by the intermediate device 37 and includes a pivot element 99, also referred to herein as a pivot pin or a cross-pin, and a tail 67, which are received, respectively, into a fulcrum 166 and a tail slot 167 defined by the receiver 96 of the coupling body 93, as described in additional detail herein.

Figure 4:
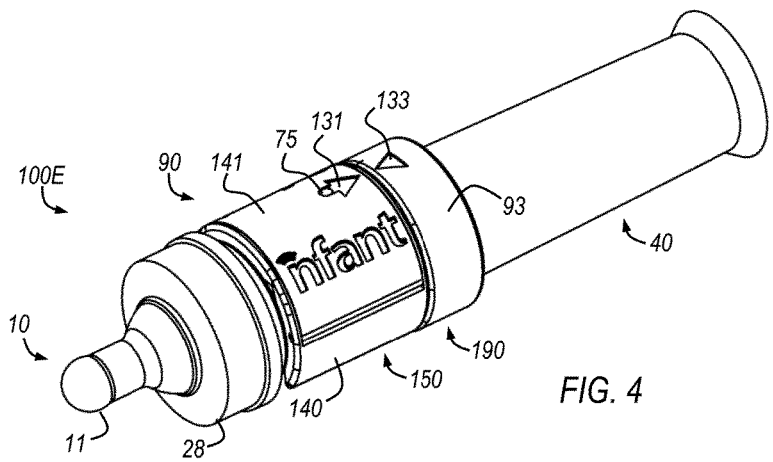
FIG. 4 is a schematic perspective illustration of another embodiment of a tongue evaluation apparatus including a coupling device.
Figure 5:
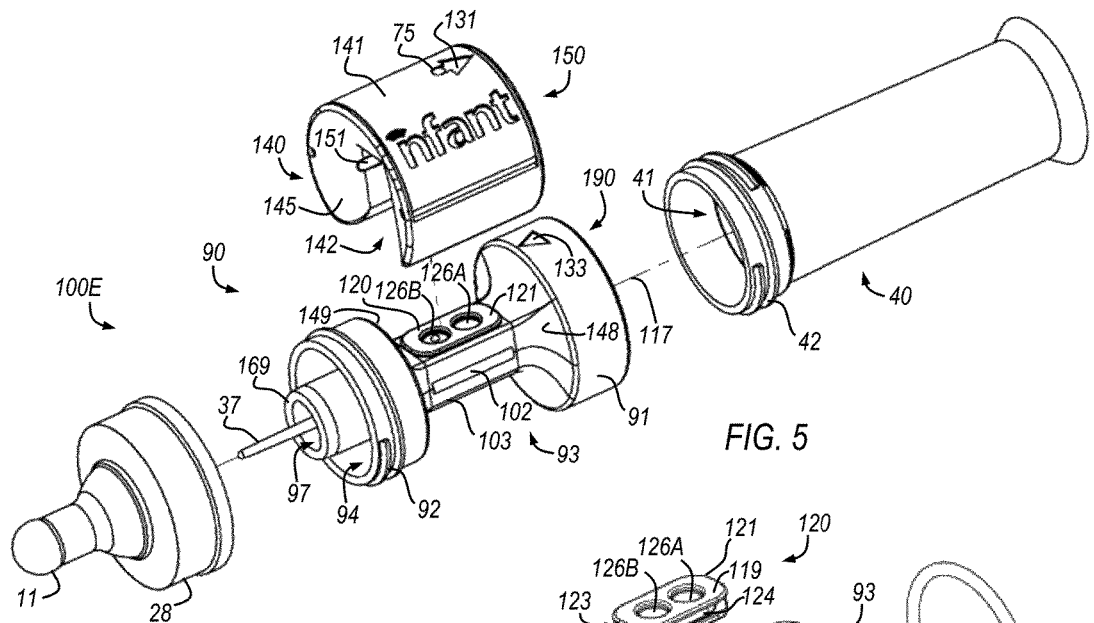
FIG. 5 is an exploded perspective view of the tongue evaluation apparatus of FIG. 4.
Figure 6:
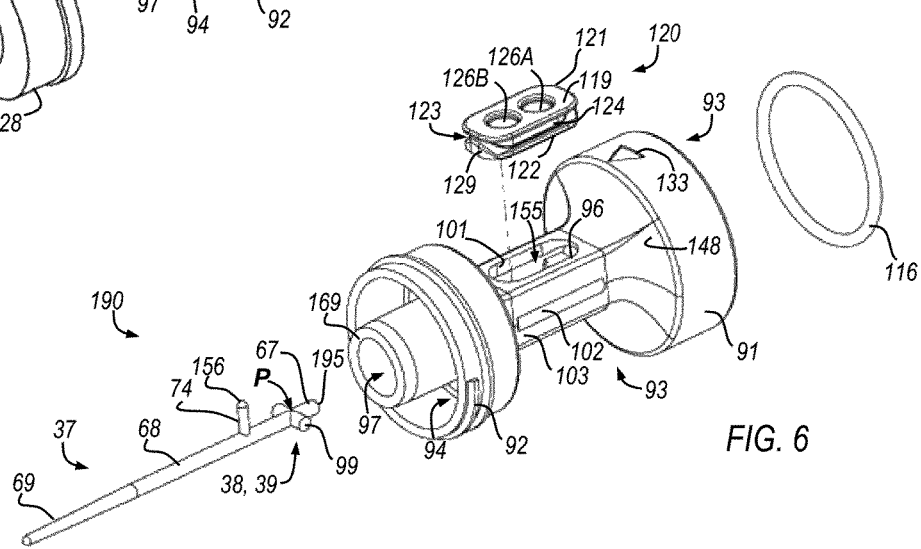
FIG. 6 is an exploded perspective view of the coupling device of FIGS. 4 and 5 including a coupling element, a pivotable insert and a sensor plug.

Referring to FIGS. 4-14, an example configuration of a tongue evaluation apparatus 100E is illustrated. As shown in FIGS. 4-6, the evaluation apparatus 100E includes a coupling device generally indicated at 90. The coupling device 90 includes a housing assembly generally indicated at 150 and a coupling assembly generally indicated at 190. The coupling assembly 190, as shown in FIG. 6, includes a coupling element generally indicated at 93, a sensor plug generally indicated at 120, and intermediate device generally indicated at 37. The intermediate device 37 is pivotably attached to the coupling element 93. As shown in FIGS. 12A-12C, the housing assembly 150 includes a housing 140 and a cover 141 operatively attached to each other, to house the sensing device 30 and the communications interface 35 (see FIGS. 12B, 12C). When the housing assembly 150 is attached to the coupling assembly in an installed position, the sensing device 30 and sensor plug 120 cooperate to provide a sensing apparatus 130 including at least one sensor 79. In the example shown, the sensing device 30 includes a first sensor 79A to sense changes in pressure within a fluid passage 97 defined by the coupling element 93, and a second sensor 79B to sense movement of the intermediate device 37, for example, in response to pivoting of a lever end 69 of the intermediate device 37 positioned in a nipple element 11, where the lever end 69 is in contact with the inner surface 17 of the nipple element 11 and is pivoted by deformation of the nipple element 11 by the tongue of a subject during a sucking event, and where pivoting the intermediate device 37 actuates the sensor 79B, as described in further detail herein.

The coupling element 93, shown in additional detail in FIGS. 7, 8 and 10A-10F, includes the first end 91, the second end 92, and a central portion 103 connecting the first and second ends. As described for FIGS. 1 and 2, the first end 91 is configured to interface with a bottle 40 defining a bottle cavity 41. The bottle 40 may be a standard feeding bottle, of the type that would be available over the counter. In the example shown, the first end 91 may define a plurality of threads for engaging the threaded end 42 of the bottle 40. A seal 116, which may be, for example, an O-ring or gasket, may be inserted between the bottle 40 and the coupling device 90 to seal the interface between the end 42 of the bottle 40 and the first end 91 of the coupling element 93. The second end 92 of the coupling element 93 is configured to receive a nipple element 11, which as previously described may be a feeding nipple or a pacifier. The nipple element 11 may be sealably retained to the second end 92, for example, by the collar 28 which may be threadably engaged to the second end 92 of the coupling element 93. The fluid passage 97 defined by the coupling element 93 is open at a first opening 168 defined by the first end 91 and is open at a second opening 169 defined by the second end 92 of the coupling element 93, such that fluid can enter the first opening 168 from, for example, the bottle 40 connected to the first end 91, and flow through the fluid passage 97 and out of the second opening 169 into cavity 19 of the nipple element 11 sealably retained to the second end 92. As used herein, the term fluid is not meant to be limiting, and is not limited to one type of fluid. For example, the fluid flowing through the fluid passage 97 may be a substance ingested by the infant during feeding, such as infant formula, water, milk, juice, etc. In a preferred example, the fluid is a non-compressible fluid.

Figure 7:
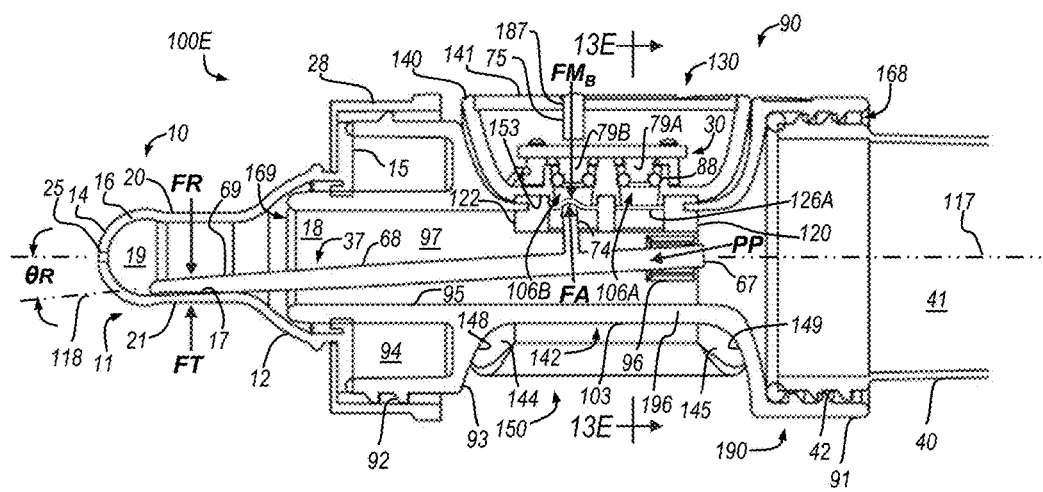
FIG. 7 is a partial cross-sectional view of the evaluation apparatus of FIGS. 4 and 5 including a sensing device and showing the pivotable insert pivoted to a first position.
Figure 8:
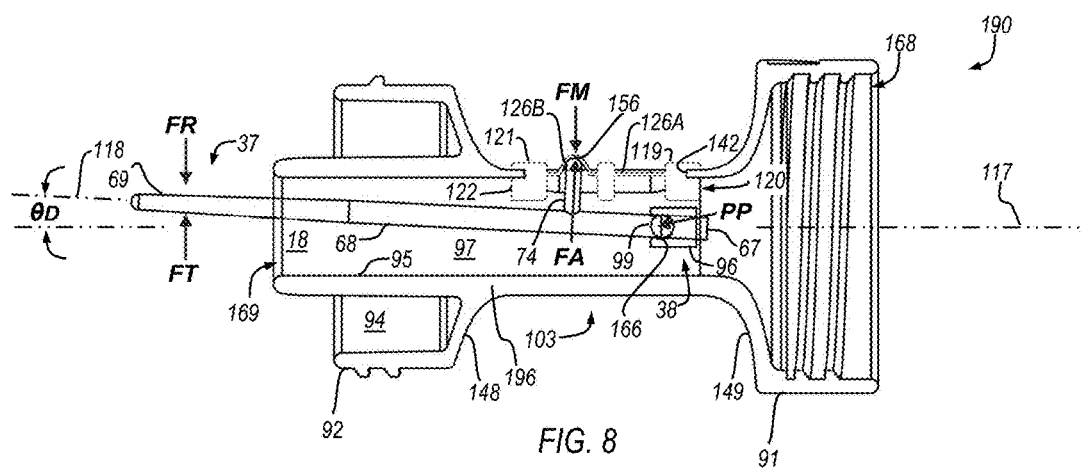
FIG. 8 is a cross-sectional view of the coupling device of FIG. 7 showing the pivotable insert pivoted to a second position.

The central portion 103 of the coupling element 93 includes an upper surface 154 (as oriented in the figures and in operation of the evaluation apparatus 100E), also referred to herein as an aperture face 154, which defines a plug aperture 155 to receive the sensor plug 120. The plug aperture 155 is further defined by an aperture lip 101 surrounding the plug aperture 155 (see FIGS. 10A, 10C and 10E). The fluid passage 97 is open at the plug aperture 155, such that the plug aperture 155 is in fluid communication with the fluid passage 97. The plug aperture 155 is configured to receive the sensor plug 120 such that the sensor plug 120 is sealably attached to the aperture face 154 and to the aperture lip 101, such that the sensor plug 120 encloses and seals the plug aperture 155 and prevents leakage of fluid from the fluid passage 97 via the plug aperture 155 to the exterior of the coupling element 93. The sensor plug 120 includes at least one membrane 126 which, with the sensor plug 120 installed in the plug aperture 155, is in fluid communication with the fluid passage 97. In the example shown, the sensor plug 120 includes a first membrane 126A and a second membrane 126B, both in fluid communication with the fluid passage 97, as shown in FIGS. 7-8. In use, the evaluation apparatus 100E is preferably filled with a sufficient volume of non-compressible fluid, e.g., infant formula, water, milk, juice, etc., such that the passage 97 is substantially filled with fluid during a feeding/evaluation session to fully submerge the membranes 126 of the sensor plug 120 when the evaluation apparatus 100E is tilted, e.g., tilted, at a feeding tilt angle β (see FIG. 14), where full submersion of the membranes 126 contributes to the accuracy and repeatability of pressure measurements made by the evaluation apparatus 100E.

The central portion 103 of the coupling element is characterized by a smaller cross-section than the first and second ends 91, 92 of the coupling element 93, such that the generally saddle-shaped housing assembly 150 can be positioned between the first and second ends 91, 92 and removably attached to the central portion 103. In the example shown, the housing assembly 150 and the coupling element 93 are shaped such that with the housing assembly 150 attached to the coupling element 93, the coupling device 90 is generally cylindrical in shape, defining a longitudinal axis 117. The generally cylindrical shape of the coupling device 90 is advantaged by being ergonomically friendly, providing ease of grasping and holding the evaluation apparatus 100 by a user during feeding of a subject, and providing a compact wireless unit which can be positioned between the bottle 40 and nipple element 11 without the need to connect to external devices during operation. The generally cylindrical shape of the coupling device 90 is not intended to be limiting, and it would be understood that other ergonomically friendly and compact external shapes for the coupling device 90 may be used. In the example shown, the aperture face 154 defining the plug aperture 155 and the adjacent side surfaces of the central portion 103 of the coupling element 93 define a rectangular portion to interface with a generally rectangular channel 142 defined by the housing 140 of the housing assembly 150 (see FIG. 9B).

Figure 9A:
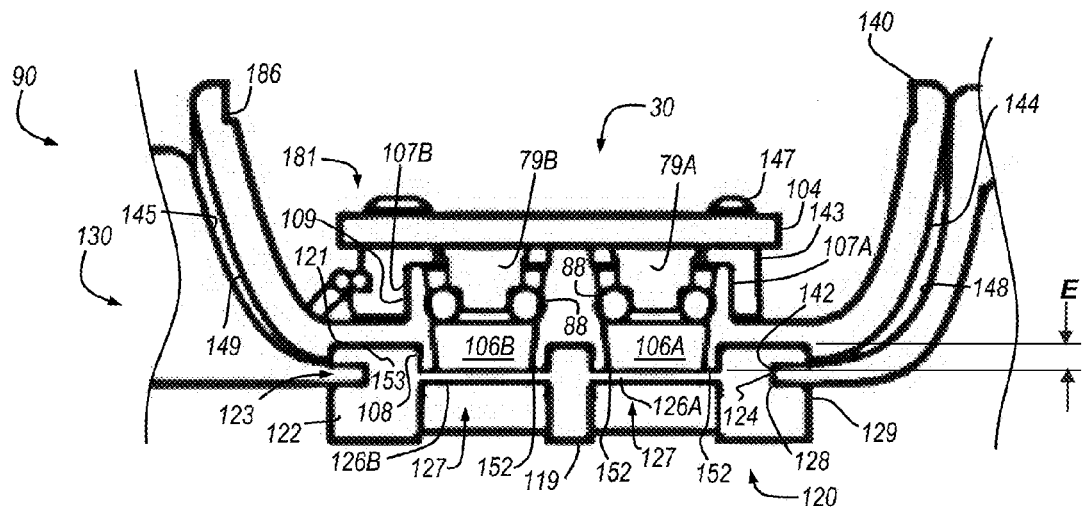
FIG. 9A is a schematic partial view of FIG. 7 showing the sensing device.

The generally rectangular channel 142 extends the longitudinal length of the housing 140, terminating at one end of the housing 140 at an opening defined by a first end surface 144 (see FIG. 13A) and terminating at the opposing end of the housing 140 at an opening defined by a second end surface 145 (see FIG. 5). The first and second end surfaces 144, 145 of the housing 140 have a contoured shape. In the example shown, and referring to FIGS. 5, 6, and 9A, the coupling element 93 defines a first coupling surface 148 extending between the central portion 103 and the first end 91, and a second coupling surface 149 extending between the central portion 103 and the second end 92 of the coupling element 93. As shown in FIGS. 7 and 9A, the first end surface 144 of the housing 140 and the first coupling surface 148 of the coupling element 93 are each contoured such that the surfaces 144, 148 have corresponding contoured shapes and are immediately adjacent each other when the housing assembly 150 is attached to the coupling assembly 190. Similarly, the second end surface 145 of the housing 140 and the second coupling surface 149 of the coupling element 93 are each contoured such that the surfaces 145, 149 have corresponding contoured shapes and are immediately adjacent each other when the housing assembly 150 is attached to the coupling assembly 190. The respective contoured shape of each of the surfaces 144, 145, 148, 149 is such that the contoured shapes facilitate alignment of the housing assembly 150 to the coupling assembly 190 during attachment of the housing assembly 150 to the coupling assembly 190. When the housing assembly 150 is attached to the coupling assembly 190, the contoured surfaces 144, 148 are immediately adjacent each other and the contoured surfaces 145, 149 are immediately adjacent each other such that the space between the adjacent surfaces 144, 148 is minimal and/or the adjacent surfaces 144, 148 contact each other, and such that the space between the adjacent surfaces 145, 149 is minimal and/or the adjacent surfaces 145, 149 contact each other, to constrain and/or prevent axial movement of the housing assembly 150 relative to the coupling assembly 190 when the housing assembly 150 is attached to the coupling assembly 190, and to axially align the sensing device 30 to the sensor plug 120, and more specifically, to axially align each of the ports 107A, 107B defined by a bridge portion 181 (see FIG. 13A) of the housing 140 with a respective one of the membranes 126A, 126B of the sensor plug 120 inserted in the plug aperture 155 of the coupling element 93.

The housing assembly 150 is removably attached to the coupling element 93 via a pair of first attachment elements 151 defined by side walls 158 of the housing 140 which are attachable to a pair of second attachment elements 102 defined by the coupling element 93. In the non-limiting example shown, the first attachment element 151 is configured as a slot, and may be referred to herein as a slot 151. The second attachment element, by way of non-limiting example, the configured as a rib, and may be referred to as a rib 102. The slots 151 are positioned on the opposing side walls 158 defining the channel 142, and the ribs 102 are positioned on opposing sides of the central portion 103 of the coupling element 93, such that the housing assembly 150 can be slid over the central portion 103 of the coupling element 93 and snapped into place by engaging the slots 151 to the ribs 102, to attach the housing assembly 150 to the coupling assembly 190 and to align the bridge portion 181 of the housing 140 to the sensor plug 120 and the aperture face 154. Likewise, the housing assembly 150 is readily removable from the coupling assembly 190 by exerting a pull force on the housing assembly 150 to disengage the ribs 102 from the slots 151. For example, the housing assembly 140 from the coupling assembly 190 when replacing the battery 77 (see FIGS. 12B, 12C and 13E) in the housing assembly 150, then re-engaged to the coupling assembly 190 for further use. The ribs 102 extend substantially along the longitudinal length of the central portion 103, such that each rib 102 is parallel to the longitudinal axis 117 of the coupling device 90. The slots 151 extend substantially along the longitudinal length of the housing 140, such that each slot 151 is parallel to the longitudinal axis 117 of the coupling device 90. The engagement of the ribs 102 and the slots 151 positively positions and longitudinally aligns the housing assembly 150 relative to the coupling assembly 190 to positively position and longitudinally align the bridge portion 181 including ports 107 to the sensor plug 120 and the aperture face 154.

Figure 9B:
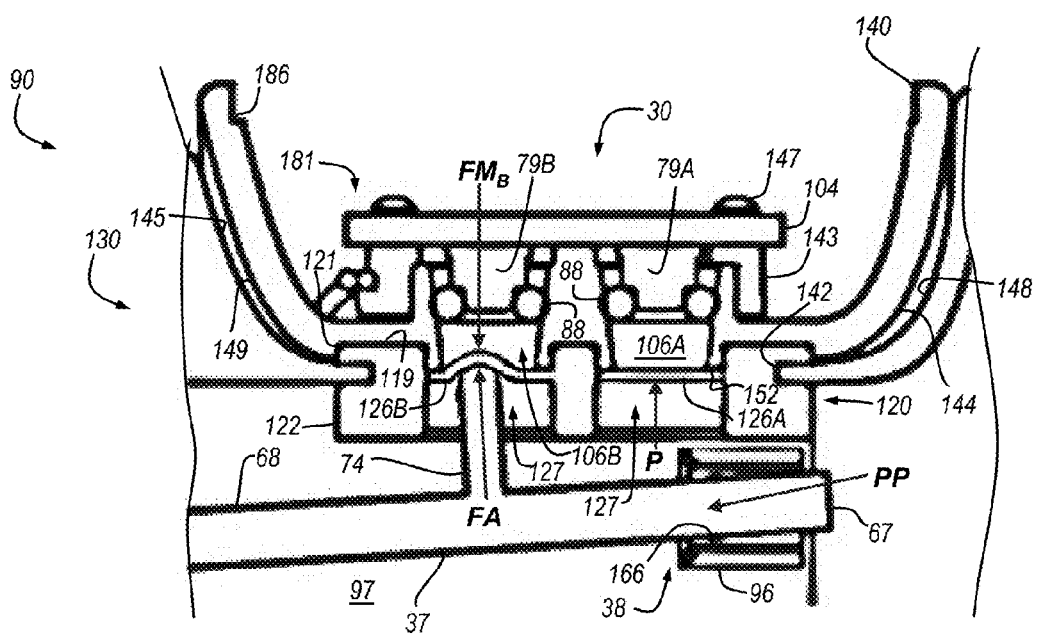
FIG. 9B is a schematic partial view of FIG. 7 showing the pivotable insert actuating the sensing device.
Figure 10A:
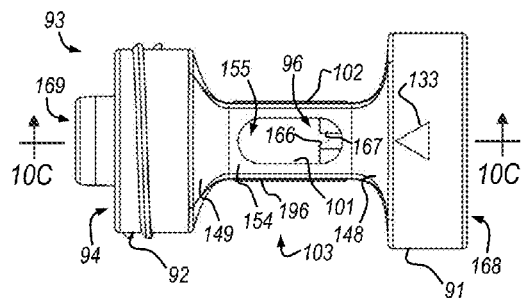
FIG. 10A is a schematic top view of the coupling element.
Figure 10B:
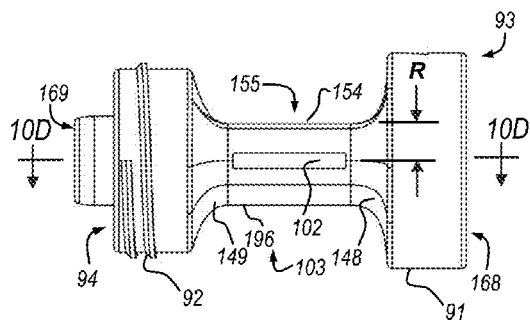
FIG. 10B is a schematic side view of the coupling element.
Figure 10C:
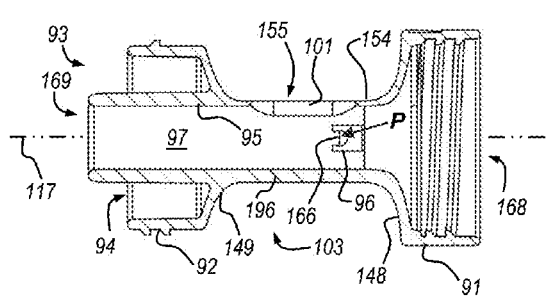
FIG. 10C is a schematic cross-sectional view of section 10C-10C of the coupling element.

As shown in FIG. 10B, each rib 102 is offset from the aperture face 154 by a rib offset distance R. As shown FIGS. 13B and 13C, the bridge portion 181 of the housing 140, in the example shown, includes a pair of ports 107, each defining an interior port end 108 terminating at a port end face 152. Each slot 151 is offset from the end face 152 by a slot offset distance S. The rib offset distance R and the slot offset distance S are configured such that in the installed position, e.g., with the housing assembly 150 attached to the coupling assembly 190, the port end face 152 of each respective port 107 is in contact with a respective membrane 126 at an engagement depth E (see FIG. 9A) which is greater than the depth X of an exterior orifice 157 partially defined by the membrane 126 (see FIG. 11D), such that the port end face 152 in contact with the membrane 126 exerts a stretching force, e.g., a pre-tensioning force, on the membrane 126, increasing the tautness of the membrane 126 and forming a sealed port chamber 106 (see FIGS. 9A and 9B) defined by the port 107, the membrane 126 and a sensor 79 disposed in the port 107. In the example shown in FIGS. 9A and 9B, a sealing element 88, such as an O-ring, is interposed between the sensor 79 and the port 107 to seal the sealed port chamber 106. The amount, e.g., the magnitude, of pre-tensioning force exerted by the port end face 152 on the membrane 126 is determined by the configuration of the port 107 and the difference between the engagement depth E and the orifice depth X. In the non-limiting example shown, the difference between the engagement depth E and the orifice depth X is defined by the position of the interior port end 108 of the housing 140 relative to position of the membrane 126 and sensor plug 120 in the coupling element 93, which is determined by the attachment of the ribs 102 and slots 151.

As described in further detail herein, the second membrane 126B exerts a membrane force FM on the actuator 74, where the magnitude of the membrane force FM is defined at least partially by the magnitude of the pre-tensioning force exerted by the port end face 152 on the second membrane 126B. It would be understood that increasing the magnitude of the pre-tensioning force exerted on the second membrane 126B increases the tautness of the membrane 126B and decreases the compliance of the membrane 126B, thereby increasing the magnitude of the membrane force FM exerted by the second membrane 126B on the actuator 74. The membrane force FM is transmitted via the actuator 74 and the intermediate device 37 as a resistive force FR exerted on the nipple element 11 via the lever end 69, such that the resistive force FR can be varied by varying the pre-tensioning force of the second membrane 126B. In a non-limiting example, the pre-tensioning force exerted by the port end face 152 on the second membrane 126B can be varied by adjusting the axial length of the interior port end 108 and/or the shape or configuration of the port end face 152, to change the engagement depth E.

In one example, each housing assembly 150 including the sensing device 30 is configured with a unique identifier, so that in use the housing assembly 150 can be identifiable to, e.g., assigned to, a single individual subject, for use only with that subject and such that data collected from that housing assembly 150 can be identified with the unique identifier and associated with the individual subject to whom that housing assembly has been assigned. In this example, the housing assembly 150 is reusable for each of a plurality of evaluation feeding sessions conducted with the assigned subject. The assigned housing assembly 150 is attached to a non-reusable coupling assembly 190 prior to each evaluation feeding session. The non-reusable coupling assembly 190, after a single use and exposure to the fluid used for the feeding session (the infant formula, juice, water, etc. flowing through the passage 97), is disposed of, and another non-reusable coupling assembly 190 is attached to the assigned housing assembly 150 for use with the assigned subject during a subsequent evaluation feeding session.

The unique identifier of the housing assembly 150 may be programmed into the software of the housing assembly 150, and retrieved wirelessly by the evaluation software 188 during initial set-up of the evaluation apparatus 100E and assignment of the specific housing assembly 150 to a specific subject. For each of a plurality of evaluation sessions conducted with the subject, the same housing assembly 150 is reused, with the device identifier being used to associate data transmitted from the housing assembly 150 with the associated subject. The arrangement of the ribs 102 and the slots 151 provides ready removal and replacement of the coupling assembly 190 from the housing assembly 150 in use. Instead of or in addition to programming the unique identifier into the software of the housing assembly 150, the unique identifier of the housing assembly 150 may be displayed on a label affixed to or otherwise marked on the housing assembly 150, in alpha-numeric characters and/or in bar code format, for example, and manually inputted and/or scanned into the evaluation software 188 for assignment of that identifier and housing assembly 150 to the respective subject. In one example, the unique identifier may be programmed into one of the boards 104, 146 and/or printed, etched or otherwise displayed on one of the boards 104, 146.

The coupling device 90 may include one or more orientating features to facilitate attachment of the housing assembly 150 to the coupling assembly 190 in the proper orientation. In the example shown, the housing assembly 150 includes a housing orienting feature 131 configured as a first arrow, and the coupling element 93 includes a coupling orienting feature 133 configured as a second arrow, such that when the arrow 131 and the arrow 133 are pointing at each other, the housing assembly 150 is properly oriented to the coupling assembly 190. The example shown is non-limiting and it would be understood that other types and configurations of orienting features 131, 133 could be used, including features of asymmetry, for example, in the contoured housing surfaces 144, 145, and the contoured coupling surfaces 148, 149, etc. to ensure proper orientation of the housing assembly 150 to the coupling assembly 190 during attachment of the housing assembly 150 to the coupling assembly 190.

Figure 10D:
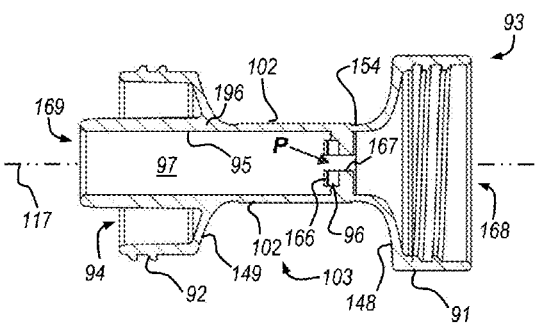
FIG. 10D is a schematic cross-sectional view of section 10D-10D of the coupling element.
Figure 10E:
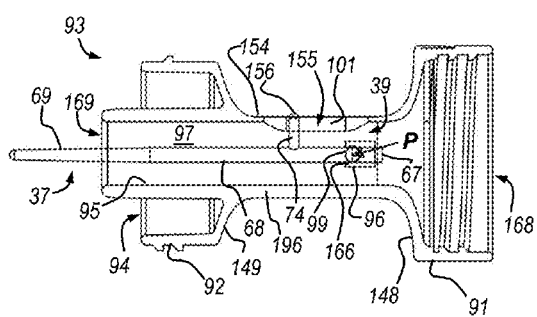
FIG. 10E is a schematic view of the coupling element of FIG. 10C including the pivotable insert.
Figure 10F:
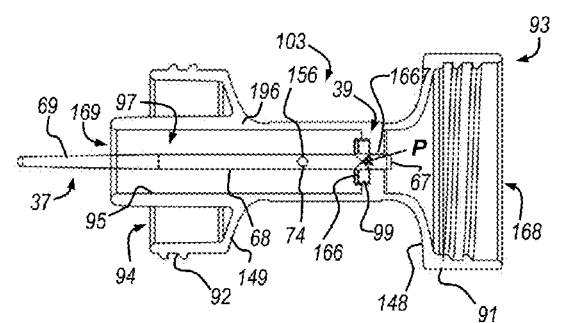
FIG. 10F is a schematic view of the coupling element of FIG. 10D including the pivotable insert.

As shown in detail in FIGS. 10A-10F, the coupling element 93 includes a receiver 96 to receive the intermediate device 37. The intermediate device 37 is configured as a lever disposed in the fluid passage 97 defined by the coupling element 93, and is pivotably attachable to the receiver 96. In the non-limiting example shown, the intermediate device 37, e.g., the lever, includes a lever bar 68 defining the lever end 69 at one end and a tail 67 at the opposing end, the tail 67 termination at a tail end 195 (see FIG. 6). The intermediate device 37 includes a pivot element 99, which in the example shown is configured as a pivot pin and may also be referred to herein as a pivot pin or a cross-pin 99. In a non-limiting example, the pivot pin 99 is transverse to the lever bar 68 and disposed between the tail 67 and the remainder of the lever bar 68. The tail 67 and the pivot pin 99 collectively define the holder 39 of the intermediate device 37 which is received into the receiver 96 to position the intermediate device 37 in the fluid passage 97 relative to the coupling element 93 and relative to the sensor plug 120. When pivotally attached to the receiver 96, the lever end 69 extends out from the second opening 169 of the fluid passage 97, such that the lever end 69 is positioned in the nipple cavity 19 as shown in FIG. 7. The receiver 96 includes the fulcrum 166 and the tail slot 167. In the example shown, the fulcrum 166 is configured as a generally cylindrical recess which is sufficiently open along its length, e.g., transverse to the longitudinal axis 117, to receive the pivot pin 99, such that the pivot pin 99 may be snapped into the cylindrical recess 166 to retain the pivot pin 99 in the cylindrical recess, e.g., in the fulcrum 166, preventing axial movement of the intermediate device 37 relative to the longitudinal axis 117, while allowing the pivot pin 99 and the lever bar 96 to pivot freely in the cylindrical recess 99, e.g., in the fulcrum 99 about a pivot point PP. When the pivot pin 99 is pivotally attached to the fulcrum 166, the tail 67 of the intermediate device 37 is positioned in the tail slot 167 defined by the receiver 96, as shown in FIGS. 10D and 10F. The tail slot 167 is configured to allow the tail 67 to pivot during pivoting of the intermediate device 37, yet is configured to prevent twisting or side to side movement of the tail 67 relative to the longitudinal axis 117. The example of a pivot element 99 configured as a pivot pin and a fulcrum 166 configured as a generally cylindrical recess defined by the receiver 96 is non-limiting, and it would be understood that the pivot element 99 and the fulcrum 166 may be shaped and/or configured otherwise to position the intermediate device 37 relative to the receiver 96 such that the intermediate device 37 is pivotable about the pivot point PP. For example, the pivot element 99 and the fulcrum 166 may be shaped and/or configured to collectively define a pivot joint such as a ball and socket joint, a saddle joint, a hinge joint, a condyloid joint, a cylindrical joint, a revolute joint, etc., such that the intermediate device 37 is pivotable about the pivot point PP. In a non-limiting example, the pivot element 99 may be located at the tail end 195 such that the tail end 195 is located in the fulcrum 166, and the intermediate device 37 is pivotable about a pivot point PP located at the tail end 195.

The lever bar 68 including the lever end 69 is substantially rigid such that the lever bar 68 does not bend in response to the deformation force FT applied to the lever end 69, to provide for direct motion transfer from the nipple 11 to the membrane 126B via the actuator post 74. In one example, the intermediate device 37 is an integral member formed of a polymeric FDA Class VI "food safe" material. In one example, the intermediate device 37 is made of thermoplastic polymer, which, by way of non-limiting example, may be one of USP Class VI acrylonitrile butadiene styrene (ABS), USP Class VI polypropylene, or the like. The examples are non-limiting, for example, the intermediate device 37 could be formed of materials having properties consistent with ABS and polypropylene, such as Cycolac®, VisiJet Flex®, PC-ISO® polycarbonate, and Accura® and like materials used in additive manufacturing.

The intermediate device 37 further includes an actuator 74, which in the example shown in FIGS. 6-8 is configured as a vertical post 74 extending from the lever bar 68 and terminating in a post end 156. The actuator 74 is positioned on the lever 37 intermediate the lever end 69 and the tail end 195, and in the example shown is positioned intermediate the pivot element 99 and the lever end 69. The actuator 74 may also be referred to herein as the actuator post 74. As shown in FIGS. 6, 7, 10E and 10F, the actuator post 74 is transverse to the lever bar 68 and perpendicular to the pivot pin 99 such that, when the intermediate device 37 is installed into the receiver 96, the post end 156 of the actuator post 74 can be pivoted in contact with one of the membranes 126. The post end 156 is generally rounded in shape and smooth, such that the post end 156 is slidably movable against the surface of the second membrane 126B such that the second membrane 126B stretches and/or is moved in a generally domed fashion with the impingement of the post end 156 and inward a sealed port chamber 106B, and such that the smooth surface of the post end 156 does not scratch or otherwise damage the second membrane 126B. The example of a generally rounded post end 156 is not limiting, and other shapes of the actuator post 74 and/or the post end 156 could be used. For example, the post end 156 could be generally shaped as a dome, button or disk having edges which are rounded, chamfered radiused or otherwise smoothed to provide a slideable interface with the second membrane 126B. As shown in FIG. 7, with the nipple element 11 in a non-deformed or resting condition, the intermediate device 37 is pivoted to a resting pivot angle $\theta_R$, such that the lever end 69 rests in contact with the inner surface 17 of the non-deformed nipple element 11. The lever end 69 in contact with, but detached from, the inner surface 17 of the nipple element 11, such that the lever end 69 can be deflected, e.g., pivoted, by deformation of the nipple element 11 between the resting pivot angle $\theta_R$ and a deflected pivot angle $\theta_D$. The post end 156 of the actuator post 74 is in sufficient contact with the second membrane 126B such that any deflection (pivoting) of the intermediate device 37 from the resting condition, e.g., from the pivot angle $\theta_R$ generates movement of the second membrane 126B, where movement of the second membrane 126B is caused (actuated) by pivoting of the post end 156 against the interior surface of the second membrane 126B. As such, there is no initial "dead zone" or space between the post end 156 and the membrane 126B which must be traversed prior to initiating movement of the second membrane 126B in response to deflection of the lever end 69 from the resting pivot angle $\theta_R$. Configuring the evaluation apparatus 100D to eliminate the "dead zone", e.g., such that the post end 156 is in contact with and/or exerting a minimal contact pressure on the second membrane 126B when the lever end 69 is in contact with the inner surface 17 of the non-deformed nipple element 11 increases the accuracy and precision of the sensing apparatus 130 to sense deflection of the lever end 69 in response to deformation of the nipple element 11 from the non-deformed state, since any deflection of the lever end 69 from the resting pivot angle $\theta_R$ generates an instantaneous corresponding movement of the second membrane 126B, and the positive positioning of the lever end 69 on the nipple inner surface 17 by the biasing force exerted by the post end 156 in contact with the second membrane 126 with the nipple element 11 in a non-deformed condition establishes a baseline from which deflection of the lever end 69 and pivoting of the intermediate device 37, e.g., the lever, by deformation of the nipple element 11 by the tongue of a subject during a suck-swallow-breathe sequence can be measured, and/or from which the evaluation apparatus 100E can be calibrated.

As shown in FIG. 8, the deformation force FT is transmitted via the lever bar 68 and is exerted as an actuator force FA by the actuator post 74 on the second membrane 126B of the sensor plug 120. The second membrane 126B exerts a resistive membrane force FM in opposition to the actuator force FA. As shown in FIGS. 7 and 8, pivoting of the lever bar 68 with sufficient force to overcome the resistive membrane force FM of the second membrane 126B causes the post end 156 to impinge on and stretch the membrane 126B, thereby changing, e.g., decreasing, the volume of the port chamber 106B adjacent the membrane 126. As shown in FIGS. 7 and 8, pivoting of the lever bar 68 away from the second membrane 126B, for example, when the deformation force FT is decreasing, causes the post end 156 to move away from the membrane 126B, thereby changing, e.g., increasing, the volume of the port chamber 106B adjacent the second membrane 126B. The resistive membrane force FM exerted by the second membrane 126B may be varied, for example, by varying the membrane thickness MTB (see FIG. 11D) of the second membrane, changing the elasticity of the material comprising the second membrane 126B, changing the engagement depth E to modify the tautness to which the second membrane 126B is stretched, e.g., pre-tensioned, by the port end face 152 in contact with the second membrane 126B, etc. thereby changing the compliance of the second membrane 126B and the resistive membrane force FM exerted by the second membrane 126B on the actuator post 74.

As shown in FIGS. 7-8, the intermediate device 37 freely pivots in the receiver 96 such that, when the lever end 69 in contact with the inner surface 17 of the nipple element 11 is deflected by deformation of the nipple element 11, for example, in response to a tongue force FT of a subject applied to the nipple element 11 during a sucking event, the intermediate device 37 is pivoted in the receiver 96 in proportion to the amount of deflection of the lever end 69 by the tongue force FT. The location of the lever end 69 at any point during a suck-swallow-breathe sequence of a sucking event may be expressed in terms of the pivot angle $\theta$. In the example shown in FIGS. 7 and 8, the origin of the pivot angle θ is the pivot point PP defined by the pivot element 99 of intermediate device 37 and the fulcrum 166 of the receiver 96, and the lever axis 118 of the intermediate device 37. In a non-limiting example, the longitudinal axis 117 of the coupling device intersects the pivot point PP and lever axis 118 of the intermediate device 37. In the example shown in FIG. 7, the nipple element 11 is in a non-deformed or resting condition, such that the lever bar 68 is pivoted downward (as shown on the drawing) away from the longitudinal axis 117 with the lever end 69 resting in contact with the non-deformed inner surface 17 of the nipple element 11 in a resting position corresponding to a resting pivot angle $\theta_R$ shown in FIG. 7. FIG. 8 shows the lever bar 68 pivoted upward (as shown on the drawing) away from the resting position, to a deflected position corresponding to a deflected pivot angle $\theta_D$. The evaluation apparatus 100E may be calibrated, by way of example, such that the resting pivot angle $\theta_R$ defines a pivot angle θ of zero degrees, and the deflected pivot angle $\theta_D$ is greater than zero degrees, as expressed relative to the resting angle $\theta_R=0$. The lever bar 68 may be pivoted to the deflected position and to the deflected pivot angle $\theta_D$, by movement of the nipple wall 16 and the inner surface 17 of the nipple element 11 during deformation of the nipple element 11 of the type shown in FIG. 3, where the magnitude of the deflected pivot angle $\theta_D$ corresponds to the deformation distance D. It would be understood that the deflected pivot angle $\theta_D$ is variable with the amount of deformation of the nipple element, such that the deflected pivot angle $\theta_D$ varies in proportion to the deformation distance D by movement and deformation of the nipple wall 16 during a sucking event.

The sensor plug 120 is shown in additional detail in FIGS. 11A through 11E. The sensor plug 120 includes a central portion 119 which defines a frame for at least one membrane 126 disposed therein. In the example shown, the sensor plug 120 includes first and second membranes 126A and 126B. The central portion 119 may be referred to herein as a frame portion 119. The sensor plug 120 includes opposing first and second flanges 121 and 122 extending outwardly from the frame portion 119. In the example shown herein, the first flange may be referred to herein as an exterior flange 121 and the second flange may be referred to herein as an interior flange 122. As used herein, the term "interior" refers to the interior of the coupling element 93 including the fluid passage 97, such that, as shown in FIGS. 7 and 8, in an installed position, the interior flange 122 of the sensor plug 120 is positioned in the interior of the coupling element 93, e.g., the interior flange 122 is positioned in the fluid passage 97 and is in communication with fluids in the fluid passage 97. As used herein, the term "exterior" refers to the exterior of the coupling element 93, such that, as shown in FIGS. 7 and 8, in an installed position, the exterior flange 121 is positioned on an exterior surface, and in the present example, is positioned on the aperture face 154 of the coupling element 93. The terms "interior" and "exterior" are not intended to be limiting, and it would be understood that other relative terms may be used to describe relative sides of the sensor plug 120. For example, the second or interior flange 122 may be referred to as being on the "measured" side of the sensor plug 120, such that the environment being measured and/or the actuators actuating the membranes 126 of the sensor plug 120 are presented to the second flange 122. The first or exterior flange 121 may be referred to as being on the sensor side of the sensor plug 120, such that the sensors 79 for detecting changes in a condition of the membranes 126 of the sensor plug 120 are presented to the first flange 121.

In the present example, the coupling element 93, and specifically, the aperture lip 101 of the coupling element 93, extends into a sealing groove 123 of the sensor plug 120 such that the interior flange 122 is separated from the exterior flange 121 by the aperture lip 101, and such that the measured environment, e.g., the fluid passage 97 and the actuator post 74, are contained by the separating element, e.g., the coupling element 93, and separated from the sensor side of the sensor plug 120 including the exterior flange 121. The sealing groove 123 of the sensor plug 120 extends the perimeter of the sensor plug 120 and is defined by a groove face 124 and the exterior and interior flanges 121, 122. In an installed position, as shown in FIGS. 7 and 8, the groove face 124 is immediately adjacent to and preferably in contact with the aperture lip 101 of the coupling element 93, the exterior flange 121 extends onto and is in contact with the aperture face 154 of the coupling element 93, and the interior flange 122 extends onto and is in contact with the inner wall surface 95 of the coupling element wall 196 immediately adjacent the plug aperture 155, such that the sensor plug 120 encloses and seals the plug aperture 155, thereby preventing any leakage of fluid from the passage 97 via the plug aperture 155. The interior flange 122, in the example shown, includes a contoured portion 129 at each of the opposing ends of the interior flange 122, where the contoured portions 129 are contoured to provide continuous contact between the interior flange 122 and the rounded inner wall surface 95 of the coupling element 93. In the example shown in FIG. 11E, a first sealing bead 128 extends continuously about the perimeter of the sealing groove 123 between the groove face 124 and the exterior flange 121, and a second sealing bead 128 extends continuously about the perimeter of the sealing groove 123 between the groove face 124 and the interior flange 122, to enclose and seal the aperture 155.

At least one membrane 126 is positioned within the frame portion 119. In the example shown, the sensor plug 120 includes a first membrane 126A and a second membrane 126B. In the installed position, the first membrane 126A is in fluid communication with the fluid passage 97 and is configured to move in response to changes in fluid pressure in the fluid passage 97. Movement of the first membrane 126A is sensed by the first sensor 79A to provide a measurement of pressure change of the fluid in the fluid passage 97. In the installed position, the second membrane 126B is positioned relative to the receiver 96 and the intermediate device 37 such that the post end 156 of the actuator post 74 is proximate to the second membrane 126B. In the example shown, the post end 156 is in contact with the second membrane 126B when the intermediate device 37 is in a resting position, e.g., when intermediate device 37 is pivoted to the resting pivot angle $\theta_R$ such that the lever end 69 is in contact with the inner surface 17 of the nipple element 11, and the nipple element 11 is in the non-deformed or resting condition. In the example shown, with the intermediate device 37 in the resting position at the resting pivot angle $\theta_R$, the post end 156 is in contact with the second membrane 126B such that the second membrane 126B exerts a baseline resistive membrane force $FM_B$ on the post end 156 to bias the intermediate device 37 to the resting position shown in FIG. 7, and such that any dead zone or open space between the post end 156 and the second membrane 126B is eliminated. The baseline resistive membrane force $FM_B$ exerted on the post end 156 is transmitted to the lever end 69 such that in the resting condition, the lever end 69 exerts a resistive force defined by the baseline force $FM_B$ (see FIG. 7) against the nipple element 11, and such that the initial resistive force FR which must be overcome by an applied tongue force FT to cause deformation of the nipple element 11 from the resting (non-deformed) condition to deflect the intermediate device 37 from the resting pivot angle $\theta_R$ is partially defined by the compliance of the nipple element 11 and partially defined by the compliance of the second membrane 126B as a determinant of the baseline resistive membrane force $FM_B$, and such that, in the configuration shown in FIGS. 4-14, the second membrane 126B functions as a compliance element 80. It would be understood that characteristics of the second membrane 126B could be varied to change the compliance of the second membrane 126B, thereby changing the magnitude of the resistive membrane force FM, exerted by the second membrane 126B on the actuator post 74, to change the effective resistive force FR exerted against the deformation force FT, e.g., exerted against the tongue of the subject during an evaluation session.

Figure 11A:
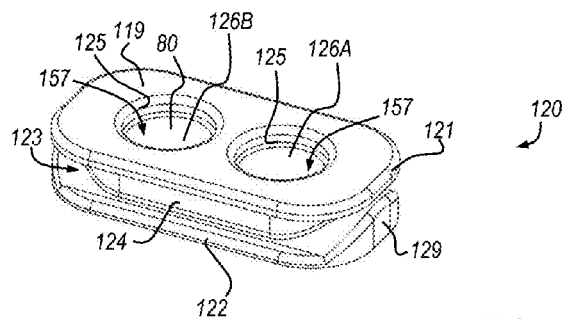
FIG. 11A is a schematic perspective view of the sensor plug.
Figure 11B:
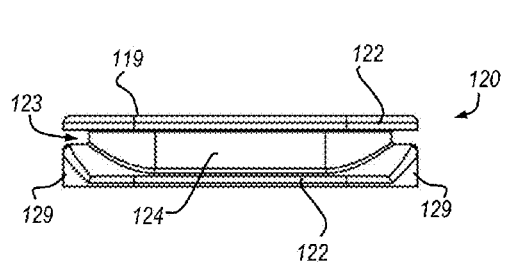
FIG. 11B is a schematic side view of the sensor plug of FIG. 11A.
Figure 11C:
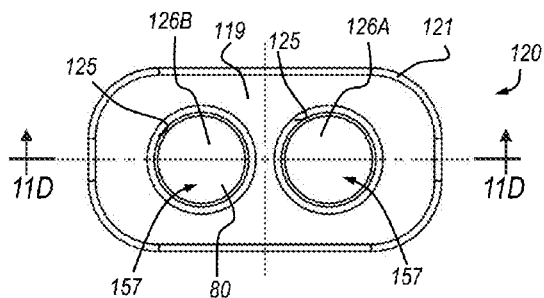
FIG. 11C is a schematic top view of the sensor plug of FIG. 11A.
Figure 11D:
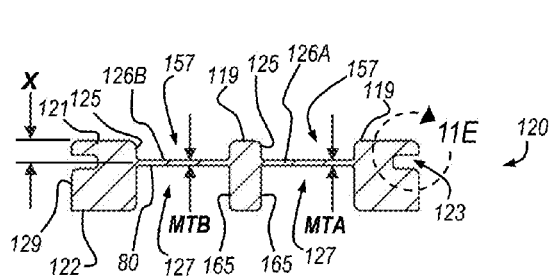
FIG. 11D is schematic cross-sectional view of the sensor plug showing section 11D-11D of FIG. 11C.
Figure 11E:
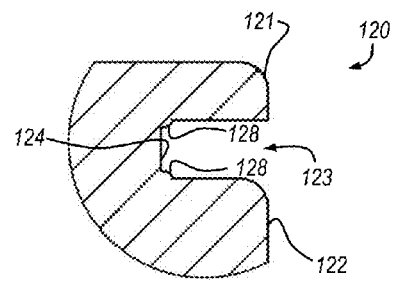
FIG. 11E is a partial schematic view of section 11C of the sensor plug shown in FIG. 11D.

As shown in FIG. 11D, each membrane 126 is characterized by a membrane thickness MT, and is disposed between the exterior and interior flanges 121, 122 to define one exterior orifice 157 and an interior orifice 127. In the non-limiting example shown in 11D, each of the membranes 126A, 126B is offset and/or recessed from the exterior surface of the exterior flange 121 by an orifice depth X, such that an exterior orifice 157 is defined by each respective membrane 126A, 126B and an annular shoulder 125 disposed between the respective membrane 126A, 126B and the exterior surface of the exterior flange 121. Likewise, the interior orifice 127 is defined by each respective membrane 126A, 126B and an annular shoulder 165 disposed between the respective membrane 126A, 126B and the interior surface of the interior flange 122, such that each of the membranes 126A, 126B is offset and/or recessed from the surface of the interior flange 122. The example shown is non-limiting and it would be understood that the membrane 126 could be substantially flush with the exterior surface of the exterior flange 121 such that the annular shoulder 125 would be minimally, e.g., such that the orifice depth X would be minimal approaching zero. In another example, the membrane 126 could be flush with the exterior surface of the exterior flange 121 such that the sensor plug 120 does not include an exterior orifice 157 or shoulder 125, such that the orifice depth X would be zero.

In a non-limiting example, the plug 120 including the membranes 126A, 126B are made of a FDA Class VI "food safe" (FS) silicone. The example is non-limiting, and other FDA Class VI FS materials, such as polyethylene and rubber-based materials such as urethane, may be used. In the example shown, the sensor plug 120 is compression molded. Other forming methods, including injection molding, could be used to form the sensor plug 120.

In the example shown, the membranes 126A, 126B have the same membrane thickness MT, such that a thickness MTA of the first membrane 126A is equal to the thickness MTB of the second membrane 126B. In a non-limiting example, the membrane thicknesses MTA and MTB are less than 0.5 mm. The thicknesses MTA and MTB may be different. For example, the thickness MTB of the second membrane 126B may be greater than the thickness MTA of the first membrane 126A, to decrease the compliance of the second membrane 126B for the purpose of increasing the resistive membrane force FM. It would be desirable to increase the resistive membrane force FM of the second membrane 126B, for example, to provide coupling assembly 190 having a relatively higher baseline resistance for therapeutic use in strengthening the tongue of a subject. The thickness MTA of the first membrane 126A may be less than the thickness MTB of the second membrane 126B, for example, to increase the sensitivity of the first membrane 126A to changes in the fluid pressure of the fluid in the passage 97. For example, a relatively thinner first membrane 126A would be relatively more reactive and/or movable in response to changes in the fluid pressure of the fluid in the passage 97.

Referring to FIGS. 7-9B, the actuator post 74 of the intermediate device 37 protrudes into the interior orifice 127 partially defined by the second membrane 126B such that the post end 156 contacts the second membrane 126B with the intermediate device 37 pivoted to the resting pivot angle $\theta_R$, as shown in FIG. 7. When the lever end 69 of the intermediate device 37 is deflected from the resting pivot angle $\theta_R$ to a deflected pivot angle $\theta_D$, for example, by deformation of the nipple element 11 as shown in FIG. 3, the depth to which the actuator post 74 protrudes into the second membrane 126B increases, causing movement of the second membrane 126B as shown in FIG. 8. Sensor 79B positioned on the exterior side of the second membrane 126B, e.g., adjacent the exterior flange 121 and/or the exterior orifice 157, is configured to sense the movement of the second membrane 126B and output a sensor signal, where the sensor signal is indicative of the amount of movement. As such, the sensor signal can be calibrated to the movement of the second membrane 126B, the deflection of the intermediate device 37 to a deflected pivot angle $\theta_D$, and the force applied to the lever end 69 to deflect the intermediate 37 to the deflected pivot angle $\theta_D$, where, when the evaluation apparatus 100D is used with a subject, the force applied to the lever end 69 is the tongue force FT of a subject applied to the nipple element 11 to deform the nipple element, for example, during a suck-swallow-breathe sequence performed by the subject during a feeding session conducted by a user of the evaluation device 100E.

In the non-limiting example shown, the sensor 79B is a pressure sensor in fluid communication with the sealed port chamber 106B partially defined by the membrane 126B, the port 107B containing the second sensor 79B, the second sensor 79B, and the sealing element 88 disposed between the second sensor 79B and the port 107B. The sealing element 88 may be referred to herein as a sensor O-ring 88. When the lever end 69 of the intermediate device 37 is deflected from the resting pivot angle $\theta_R$ to a deflected pivot angle $\theta_D$, the depth to which the actuator post 74 protrudes into the second membrane 126B increases, causing movement of the second membrane 126B as shown in FIG. 8 which decreases the effective volume of the sealed port chamber 106B, increasing the pressure in the sealed port chamber 106B. In the example shown, the fluid contained in the sealed port chamber 106B is air, although other fluids including other gases or liquids, could be used. The pressure within the sealed port chamber 106 (each of chambers 106A, 106B) may also referred to herein as the chamber pressure, to distinguish the pressure sensed in the sealed port chamber 106 from the fluid pressure of the fluid in the passage 97. The pressure sensor 79B senses the change in chamber pressure in the sealed port chamber 106B, and outputs a pressure signal which corresponds to the change in chamber pressure, and as such corresponds to the movement of the second membrane 126B due to intrusion of the actuator post 74 by deflection of the lever end 69 of the intermediate device 37.

Still referring to FIGS. 7-9B, the first membrane 126A and the interior orifice 127 partially defined by the first membrane 126A is in fluid communication with the passage 97 defined by the coupling element 93, such that changes in fluid pressure P of fluid in the passage 97 cause movement of the first membrane 126A. The sensor 79A positioned on the exterior side of the first membrane 126A, e.g., adjacent the exterior flange 121 and/or the exterior orifice 157, is configured to sense the movement of the first membrane 126A and output a sensor signal, where the sensor signal is indicative of the amount of movement of the first membrane 126A. As such, the sensor signal can be calibrated to the movement of the first membrane 126A, and the fluid pressure P of the fluid in the passage 97, where, when the evaluation apparatus 100D is used with a subject user, the fluid pressure P of the fluid in the passage 97 changes with changes in the tongue force FT of a subject user applied to the nipple element 11 to deform the nipple element, for example, during a suck-swallow-breathe sequence performed by the subject user, where the suck-swallow-breathe sequence will cause changes in the fluid pressure of the fluid in the passage 97. During nutritive sucking (NS), the fluid may include a liquid such as water, infant formula, milk, juice, etc. to be ingested by the subject user and delivered to the aperture 25 in the nipple element 11 via the passage 97 from a bottle container 40 sealably attached to the coupling device 90. During non-nutritive sucking (NNS) the fluid may be a liquid or gas or combination of these contained in the sealed apparatus chamber defined by the passage 97, the cavity 19 of the nipple element 11, and the cavity 41 of the bottle 40, where the nipple element 11 and the bottle 40 are sealably attached to the coupling device 90 to form the sealed apparatus chamber including the passage 97. In the example of non-nutritive sucking (NNS), the nipple element 11 may be a pacifier defining a nipple cavity 19 and sealably attached to the coupling device 90.

In the non-limiting example shown, the sensor 79A is a pressure sensor in fluid communication with a sealed port chamber 106A partially defined by the first membrane 126A, the port 107A containing the first sensor 79A, the second sensor 79B, and a sensor O-ring 88 disposed between the first sensor 79A and the port 107A. When the fluid pressure P of the fluid in the passage 97 changes, the change in fluid pressure P causes movement of the first membrane 126A. For example, when the fluid pressure P of the fluid in the passage 97 increases, the increasing fluid pressure P increases the tension of the first membrane 126A, causes deflection, e.g., movement and/or stretching of the first membrane 126A outward from the passage 97 and into the sealed port chamber 106A, which decreases the effective volume of the sealed port chamber 106A, increasing the chamber pressure in the sealed port chamber 106A. In the example shown, the fluid contained in the sealed port chamber 106A is air, although other fluids including other gases or liquids, could be used. The pressure sensor 79A senses the change in chamber pressure in the sealed port chamber 106A, and outputs a pressure signal which corresponds to the change in the fluid pressure P of the fluid in the passage 97.

As shown in FIGS. 7, 9A and 9B, and in additional detail in FIGS. 12A-13E, the sensors 79A and 79B are included in the sensing device 30 housed in the housing assembly 150. The sensing device 30 in combination with the sensor plug 120 comprises the sensing apparatus 130. The sensing device 30 is in communication with a communications interface generally indicated at 35 in FIG. 12B, and is electrically connected to the power source 77 via a connector generally indicated at 29. The sensing device 30, power source 77 and communications interface 35 are operably attached to or positioned within the housing 140, which is enclosed by the cover 141 to form the housing assembly 150. The cover 141 is generally semi-cylindrical in shape, as shown in FIG. 12B and is attached, in the non-limiting example shown, to the housing 140 with a plurality of cover fasteners 184, which may be screws, pins, etc. In the example shown, the cover 141 may be hingedly attached to the housing 140 by means of one or more hinges 185, such that the cover 141 may be hinged open during, for example, replacement of the battery 77, by removal of one or more of the cover fasteners 184. The cover 141 and the housing 140 are preferably configured such that the housing assembly 150 is a sealed unit. As shown in FIGS. 12B and 12C, the housing 140 includes a cover interface 186, which in the non-limiting example is shown is configured as a shoulder or ridge to which the cover 141 interfaces to seal the housing assembly 150. The example of attaching the cover 141 to the housing 140 by cover fasteners 184 is non-limiting, and other configurations of a cover 141 and/or cover interface 186 may be used. For example, the cover 141 and housing 140 may be formed or shaped such that the cover 141 is removably attachable to the housing 140 via a tabbed arrangement, a combination of integrally formed pins and holes, slots and grooves, etc. without the use of cover fasteners 184. The cover 141 and the housing 140 are made of an FDA Class VI "food safe" (FS) material. In a non-limiting example, the cover 141 and housing 140 are each made of a moldable thermoplastic polymer such as USP Class VI FS acrylonitrile butadiene styrene (ABS) or USP Class VI FS polypropylene.

Figure 15:
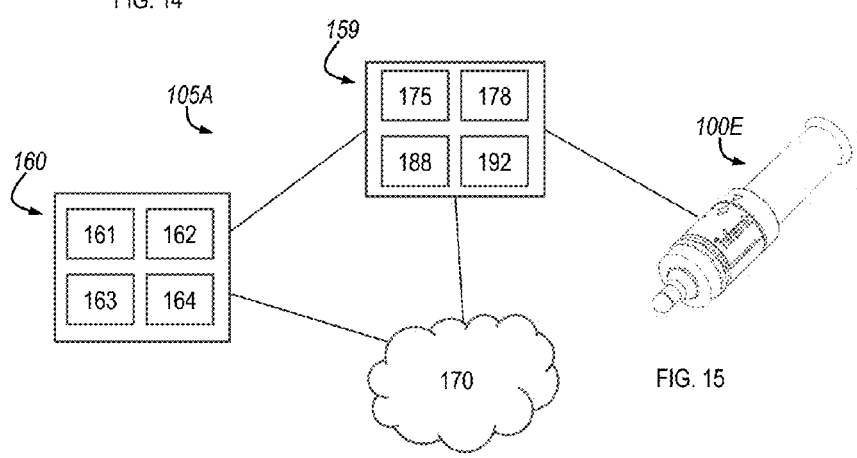
FIG. 15 is a schematic illustration of a system for evaluating tongue movement including the evaluation apparatus of FIG. 4 and a mobile device.

The cover 141 includes a window 187 for viewing of a user interface element 75, as shown in FIGS. 7, 12A and 12B. In the non-limiting example shown, the user interface element 75 is configured as a light emitting diode (LED) which is operably connected to the communications interface 35 such that the user interface element 75 is viewable through a window 187 defined by the cover 141. The LED may be configured to indicate different colors and to blink at various blink rates including a constant on or off condition. The window 187 may be sealed, to seal the cover 141, or may be configured such that when the LED is fitted to the window 187, the LED sealably interfaces with the window 187 to seal the cover 141. The communications interface 35 may be programmed to actuate the user interface element 75 to provide light indications to a user of the evaluation apparatus 100E as to the operating status of the evaluation apparatus 100E. For example, the user interface element 75 may remain in an unlit or "off" status to indicate the coupling device 90 is in one of an immobile condition, has no battery 77 installed, has woken-up but failed to pair with a mobile device 159 within an allotted time frame, and/or has timed out after a feeding session of a subject has been conducted using the coupling device 90. The mobile device 159, as shown in FIG. 15, includes the tongue evaluation application 188 stored to the device memory 178, where the mobile device 159 and the coupling device 90 have been configured for wireless pairing and communication using a wireless protocol such as Bluetooth® Low-Energy, and the tongue evaluation application 188, also referred to herein as the evaluation application 188, is configured to collect, analyze, transmit and/or store data received wirelessly from the sensing apparatus 130 of the coupling device 90.

By way of non-limiting example, the user interface element 75 may display a first color and blink at a first blinking rate, for example, display red and blink slowly, to indicate the coupling device 90 is "on," e.g., woken up, but not yet paired with the mobile device 159, and/or the user interface element 75 may return to the first color and first blinking rate after a feeding session with a subject has been completed and the coupling device 90 has been deactivated from tongue evaluation application 188. The user interface element 75 may display a second color and a first blinking rate, for example, display green and blink slowly, to indicate the sensing apparatus 130 has paired with the evaluation application 188, and is awaiting user activation, or is paused during data streaming from the coupling device 90 to the mobile device 159. The user interface element 75 may display the second color and be lit but not blinking, e.g., display green and glow solid, to indicate the feeding session has been initiated by the user, e.g., a subject is being fed by the user using the evaluation apparatus 100E, data is being streamed from the sensing apparatus 130 to the mobile device 159 during the feeding session, feeding is resumed from a paused condition and/or data streaming is resumed when feeding is resumed. The user interface element 75 may display the first color and a second blinking rate, for example, display red and blink fast, to indicate the coupling device 90 has moved out of range of the mobile device 159 during streaming of data, or streaming of data from the coupling device 90 to the mobile device 159 has been otherwise interrupted. The user interface element 75 may display the first color and be lit but not blinking, e.g., display red and glow solid, to indicate the energy supplied by the power source 77 is low at activation or after feeding, e.g., to indicate the power supplied by the battery 77 is low and replacement of the battery 77 is required, where a low power supply may prevent wireless communication and/or data streaming between the coupling device 90 and the mobile device 159. The examples provided herein are illustrative and non-limiting, and it would be understood that other light configurations, color and blink rate combinations, etc., may be used as light indications of the various operating states and conditions of the coupling device 90. For example, the user interface element 75 may be configured to provide a light indication, using a combination of color and blink rate, to indicate the evaluation apparatus 100E is off tilt, e.g., off center, to alert the user to tilt the evaluation apparatus 100E, as shown in FIG. 14, to reestablish the orientation of the evaluation apparatus 100E at a predetermined target tilt angle $\beta_{target}$. The user interface element 75 and window 187 may be otherwise configured. For example, the user interface element 75 may be configured to include a display capable of displaying graphical images and/or alpha-numeric text to a user to indicate the various operating states and conditions of the coupling device 90 and/or to display other information such as a device identifier unique to that specific coupling device 90 to identify the coupling device 90 as corresponding and/or being assigned to a specific subject. The device identifier may be, for example, a serial number or a scannable bar code of the specific coupling device 90 which may be displayed by the user interface element 75 on the coupling device 90 or packaging accompanying the coupling device 90, such that the device identifier is retrievable from the coupling device 90, for example, for input to the evaluation application 188 during pairing of the coupling device 90 with the specific subject.

Still referring to FIGS. 12A-13E, the housing 140, as described previously, is configured to be removably attached to the central portion 103 of the coupling element 93, via the slots 151 defined on opposing side walls 158, where the side walls 158 and the bridge portion 181 define the channel 142. The housing 140 may be integrally molded to provide the housing body 140 shown in FIGS. 13A-13D, and in perspective in FIGS. 12B and 12C. The housing 140 includes a bridge portion 181 which is intermediate the side walls 158 and is intermediate the first and second contoured housing surfaces 144, 145. The bridge portion 181 includes, in the example shown, a plurality of retaining elements 143 configured to receive sensor fasteners 147 to fasten the sensor board 104 to the bridge portion 181. The sensor fasteners 147 are inserted into holes 189 in the sensor board 104 and fastened to the retaining elements 143, where the retaining elements 143 and holes 189 are arranged to position the sensor board 104 relative to the bridge portion 181, and specifically to position each of the sensor elements 79A, 79B mounted to the sensor board 104 relative to the respective ports 107A, 107B defined by the bridge portion 181. The housing 140 includes a battery cavity 182 adjacent one of the side walls 158 and a board cavity 183 adjacent the other of the side walls 158. In the example shown, the communications interface 35, which includes a communications board 146 to which various elements are mounted, is positioned in the board cavity 183. A board locator 194, which may be integral to the housing 140, may be positioned in the board cavity 183. In the example shown, the board locator defines a slot for receiving the communications board 146 to position and retain the communications board 146 in the board cavity 183.

The battery cavity 182 is configured to receive a battery connector 29 and a battery 77. A battery locator 193, which may be integral to the housing 140, may be positioned in the battery cavity 183, and configured to position and/or retain battery contacts 136 and/or the battery 77. In the example shown, the battery 77 is a coin cell battery, also known as a button battery, which is inserted to the battery contact clip 136 to provide power to the electronics and/or componentry of the communications board 35 and the sensor board 104. A coin cell battery 77 of the type shown in FIG. 12C can typically have a shelf life of 5 years prior to initial use, and is estimated to provide sufficient power to stream data continuously from the coupling device 90 for approximately 21 hours before a battery change, e.g., a replacement coin cell battery 77, is required. In the example shown, the coin cell battery 77 powers data streaming from the communications interface 35 continuously at a selective frequency. In one example, data is streamed using Bluetooth® Low-Energy at 16 Hertz (Hz). In another non-limiting example, data is streamed using Bluetooth® Low-Energy at 30 Hertz (HZ). The battery 77 is readily replaced by opening and/or removing the cover 141 to access the battery 77 for removal and replacement. The battery connector 29 includes a battery terminal 138 which is electrically connected to the battery contact clip 136. The battery terminal 138 is electrically connectable to a terminal connector 139, which in the example shown is located on the communications board 146, to conduct power to the communications board 146. The communications board 146 is electrically connected to the sensor board by a cable 89, such that power can be provided from the battery 77 through the communications board 146 and cable 89 to the sensor board 104. The cable 89 includes a plurality of circuits, such that the cable 89 is configured to conduct power from the battery 77 to the sensor board 104, and is configured to transmit signals from the sensors 79A, 79B to the communications board 146 for wireless transmission, for example, by a communications module 132 to a mobile device 159 paired to the coupling device 90. The cable 89 may include other circuits, for example, for control of the LED user interface 75, for communication with an accelerometer 134 included in the coupling device 90, etc. The example shown in the figures is non-limiting, and it would be understood that other types of power sources 77 could be used to provide power to the sensor board 104 and the communications board 132. For example, the housing assembly 90 may be adapted to be plugged into a ground source of electricity for recharging of a rechargeable power cell 77, or to be powered directly from the ground source of electricity, where the ground source of electricity may be, for example, an electrical outlet connected to the power grid, or provided via an intervening device. For example, the housing assembly 90 may be configured for connection to the mobile device 159, via a USB port or the like, such that the power source 77 is provided via the mobile device 159 and/or is recharged via the connection with the mobile device 159.

The communications interface 35 includes the communications module 132 which is operatively attached to the communications board 146. The communications module 132 is configured as a wireless module for transmitting data including sensor signals generated by the sensors 79A, 79B, to a communications interface 135 of the mobile device 159, as shown in FIG. 15. In a non-limiting example, the communications module 132 is configured to transmit data via Low-Energy Bluetooth®, e.g., Bluetooth 4.0®, Smart Bluetooth®, Bluetooth LE® and similar, to the mobile device 159, where the data is received by the communications interface 135 and/or is transmitted to the evaluation application 188 installed on the mobile device 159. The data may be displayed on the mobile device 159 on the display 175 of the mobile device 159 for viewing by a user. The use of Low-Energy Bluetooth® to transmit data wirelessly is advantaged by enabling transmission of substantial amounts of data at very low power consumption, such that the coupling device 90 can be powered by a low cost and compact energy source such as the coin cell battery 77 for multiple evaluation sessions without having to replace the coin cell battery 77. Further, the use of the non-rechargeable coin cell battery 77, which does not require recharging or access to a ground source of electricity for use, allows for the use of the evaluation apparatus 100E in remote or field locations where replacement coin cell batteries 77 can be provided however a ground source of electricity may not be readily available.

The coupling device 90 may also include the accelerometer 134, which in the example shown may be electrically connected to the communications board 146. The example is non-limiting, and the accelerometer 134 may be located elsewhere within the coupling device 90, for example, on the sensor board 104 or in a location within the housing 140 where the accelerometer 134 can be oriented relative to the housing 150, powered by the power source 77, and in communication with the communications module 132 such that data can be transmitted from the accelerometer 134 to the communications module 132 and via the communications module 132 to the mobile device 159. In one example, the accelerometer 134 is a small, low-power, 3-axis linear programmable accelerometer such as an Xtrinsic® FXLS8471Q accelerometer or the like. The accelerometer 134 is configured to detect the apparatus tilt angle β of the evaluation apparatus 100E, where, in a non-limiting example shown in FIG. 14, the tilt angle β measures the orientation of the evaluation apparatus 100E relative to a horizontal axis 191, including the pitch, yaw and/or roll of the evaluation apparatus 100E relative to the horizontal axis 191. The tilt angle β, in one example, can be measured and output to the mobile device 159 for display, as shown in the example display 175 illustrated in FIG. 16. In the example shown, a measured or actual tilt angle $β_{actual}$ of the evaluation apparatus 100E can be compared with a minimum or target tilt angle $β_{target}$ which has been established or predetermined for the evaluation apparatus 100E, and feedback provided to the user to adjust the tilt angle β of the evaluation apparatus 100E from the current measured tilt angle $β_{actual}$ to the target tilt angle $β_{target}$, e.g., in the illustrated example, in the exemplary display 175 in FIG. 16, feedback is provided to "tilt upward" the evaluation apparatus 100E to adjust the orientation of the evaluation apparatus 100E to the target tilt angle $β_{target}$. The target tilt angle $β_{target}$ may be determined as the angle required to optimize orientation of the evaluation apparatus 100E for feeding of the subject, to provide a flow of fluid to the nipple 11, and fluid in the passage 97 in contact with the sensor plug 120 and/or plug membranes 126A, 126B in sufficient volume to submerge the interior flange 122, filling the interior orifices 127 of the sensor plug 120 with fluid such that the membranes 126A, 126B are fully covered by the fluid, where completely covering the membranes 126A, 126B with the volume of non-compressible fluid optimizes the accuracy of measurements of fluid pressure changes within the apparatus chamber defined by the nipple cavity 19, passage 97 and bottle cavity 41. In the example shown, the target tilt angle $β_{target}$, e.g., the minimum preferred tilt angle, is 45 degrees. The accelerometer 134 may include auto-awake and return to sleep functions, which may be enabled and/or programmed to save power consumption of the battery 77 when the evaluation apparatus 100E is not in use and/or is not transmitting data. The accelerometer 134 may include pulse and/or tap detection which may be programmed for example, such that the evaluation apparatus 100E may be turned "on" and/or woken up by a user tapping the coupling device 90 and/or evaluation apparatus 100E in a predetermined pattern. In one example, the coupling device 90 is programmed to wake up in response to a double tap of the coupling device 90 by a user.

Referring to FIGS. 12A-12C, in the example shown, the sensor board 104 includes first and second sensors 79A and 79B, which are arranged on the sensor board 104 for positioning in the respective first and second ports 107A and 107B to form the respective sealed port chambers 106A, 106B when the housing assembly 150 is attached to the coupling assembly 190, e.g., when the bridge portion 181 of the housing 140 interfaces with the sensor plug 120. In the example shown, each of the sensors 79A, 79B is configured as a pressure sensor for detecting changes in chamber pressure, respectively, in each of the sealed port chambers 106A, 106B caused respectively, by movement of each of the membranes 126A, 126B. Changes in the chamber pressure of the air in the first sealed port chamber 106A sensed by the first pressure sensor 79A are proportional to movement of the first membrane 126A in response to changes in fluid pressure P of the fluid in the passage 97 in contact with the membrane 126A, such that the sensor signals from the first pressure sensor 126A can be correlated to pressure changes in the fluid pressure P of the fluid in the passage 97 during a feeding session and corresponding to changes in pressure during suck-swallow-breathe (SSB) cycles occurring during the feeding session. Changes in the pressure of the air in the second sealed port chamber 106B, e.g., the chamber pressure, sensed by the second pressure sensor 79B, are proportional to movement of the second membrane 126B in response to the actuation force FA exerted on the second membrane 126B by the actuator port 74 by deflection of the lever end 69 causing the intermediate device 37 to pivot about the pivot point PP, where the pivot angle θ to which the intermediate device 37 is pivoted and the actuation force FA is proportional to the deformation distance D to which the nipple element is deformed by the tongue force FT exerted by the tongue of the subject during a feeding session, such that the sensor signals from the second pressure sensor 126B can be correlated to the deformation distance D and to the tongue force FT to quantify tongue strength and coordination of the subject. In the present example, the pressure sensors 79A, 79B are capable of measuring pressures in the sealed port chambers 106A, 106B at a resolution of 0.02 milli-bar (mbar) and an accuracy of +/−2 mbar, which can be increased to an accuracy of +/−1 mbar with single point calibration/zero offsetting, such that changes in the deflection of the lever end 69 can be sensed with a resolution of 0.001 mm. The example is non-limiting, and it would be understood that other types of sensors, for example, infrared, electrical, mechanical (force, stress, strain), electromagnetic, optical, and/or acoustic type sensors could be used and/or configured as the sensor 79 for detecting movement of the respective membrane 126. The sensor board 104 may include at least one transducer 76 for converting the sensor signals received from the sensors 79A, 79B to output signals which are provided to the communications interface 35 for output as electrical data signals to the mobile device 159. A sensor sealing element 88, which in the present example is an O-ring or similar annular seal, is positioned on each sensor 79A, 79B to seal the sensor 79A, 79B to the respective port 107A, 107B, as shown in FIGS. 9A and 9B.

Figure 13A:
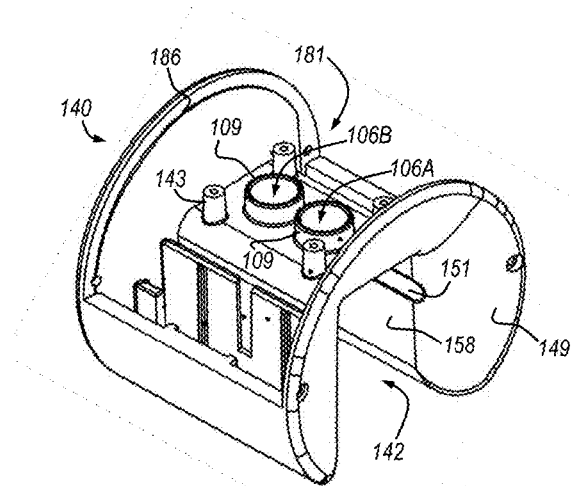
FIG. 13A is a schematic perspective view of the housing of FIG. 12A.
Figure 13B:
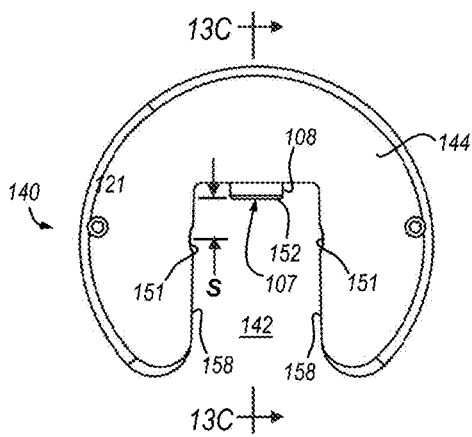
FIG. 13B is a schematic end view of the housing of FIG. 13A.
Figure 13C:
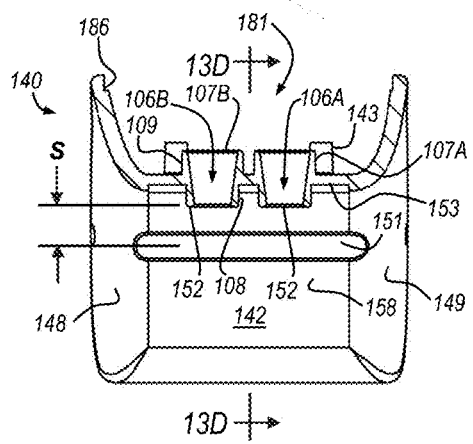
FIG. 13C is a schematic cross-sectional view of section 13C-13C of the housing of FIG. 13B.
Figure 13E:
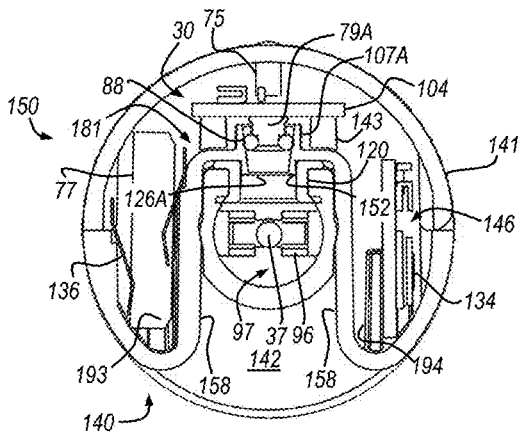
FIG. 13E is a schematic cross-sectional view of section 13E-13E of the coupling device.
Figure 13D:
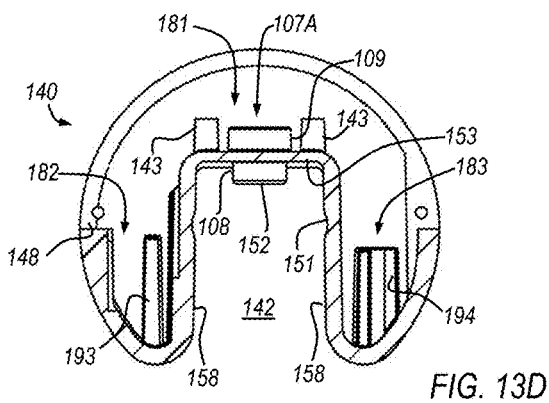
FIG. 13D is a schematic cross-sectional view of section 13D-13D of the housing of FIG. 13C.

The configuration of the bridge portion 181 and the ports 107 is shown in additional detail in FIGS. 13A-13D, and the interface between the bridge portion 181, the ports 107 and the sensor plug 120 when the coupling assembly 190 is attached to the housing assembly 150 is shown in detail in FIGS. 9A, 9B and 13E. As shown in FIGS. 13A-13D, each port includes an interior port end 108 protruding from a recessed interior surface 153 of the bridge portion 181, and an exterior end 109 protruding from the exterior surface of the bridge portion 181. The port chamber 106 defined by each port 107 is tapered from the exterior end 109 to the interior end 108, as shown in FIG. 13D, to facilitate sealing of the sensor 79 to the port 107. As shown in FIGS. 9A, 9B and 13E, the sensor O-ring 88 is disposed between the sensor 79 and the inner surface of the port 107 defining the port chamber 106, such that the sensor O-ring 88 is compressed between the sensor 79 and the tapered surface by attachment of the sensor board 104 to the retaining elements 143 by the sensor fasteners 147, to seal the port chamber 106 at the exterior end 109 of the port 107.

When the coupling assembly 190 is attached to the housing assembly 150 by attachment of the ribs 102 to the slots 151, the recessed interior surface 153 of the bridge portion 181 interfaces with the sensor plug 120 to exert a compressive force on the exterior flange 121 of the sensor plug 120, to seal the sensor plug 120 to the housing 140, and to position the port end faces 152 of each of the ports 107A, 107B in contact with the respective membranes 126A, 126B at the engagement depth E, as previously described, such that the port end face 152 in contact with the membrane 126 seals the port chamber 106 at the interior end 108 of the port 107.

Referring now to FIG. 15, the tongue evaluation system 105A is shown. The evaluation system 105A and evaluation apparatus 100E can be used with a subject in a noninvasive manner to accurately collect, model and quantify the tongue movement, tongue force, and/or sucking behavior of a subject, which may include determining the deformation forces exerted by the subject on the nipple element 11 during an evaluation feeding sequence, during which the subject may perform one or more suck-swallow-breathe (SSB) sequences. Both NS and NNS evaluation sessions may be used to evaluate a subject. The evaluation system 105A includes the evaluation apparatus 100E, configured in a non-limiting example as previously described herein. The evaluation apparatus 100E is in communication with the mobile device 159, such that signals, data, information etc. can be transmitted between the evaluation apparatus 100E and the mobile device 159. In the example shown, the evaluation apparatus 100E and the mobile device 159 are connected wirelessly via the wireless communications module 132 in the evaluation apparatus 100E, where the communications module 132 uses low energy Bluetooth® such that substantial amounts of data may be streamed to and from the coupling device 90 to the mobile device 159 with minimal power consumption from the battery 77.

The mobile device 159 includes the device communications interface 135, the user interface 175 configured to display information including data, analysis results, messages, etc. to a user, a CPU/processor 192 and the memory 178. Each of the device communications interface 135, the user interface 175, and the CPU/processor 192 may include and/or be in operative communication with the memory 178, which may be configured as one or more of Read Only Memory (ROM), Random Access Memory (RAM), electrically-erasable programmable read only memory (EEPROM), etc., of a size and speed sufficient for executing the functions performed by the respective communications interface 135, the user interface 175, and the CPU/processor 192, to store and execute applications used in performing the functions of the evaluation system 105A, including, for example the tongue evaluation application 188, and to store data in one or more databases. The collected and/or stored data may be analyzed for evaluation and measurement of the tongue movement and/or tongue force FT exerted by the subject on the instrumented nipple 10 during suck-swallow-breathe (SSB) cycles, from which measurements of tongue strength and coordination such as work performed, impulse, power, sucking frequency, rate of force production, rate of tongue movement, deformation distance, or other strength and coordination measures may be derived. Analysis may include evaluation of sucking frequency and/or rate, rate of exerted force (exerted force measured over time), deformation rate (deformation distance over time) or other parameters measured over the time period of the sucking session which may be used, for example, to quantify fatigue. The configuration shown in FIG. 15 is not intended to be limiting, and it would be understood that functions performed by each of the elements 175, 192, 178, 135 may be performed by another of the elements 175, 192, 178, 135 as configured to do so. The mobile device 159 may be, by way of non-limiting example, a portable computer (PC), a laptop, a tablet computer such as an Android™ tablet or an iPAD®, a handheld PC, a personal digital assistant (PDA), a smart phone such as an Android™ phone or an iPhone®, or other small computing device, or the like. In the non-limiting example shown, the system 105A is operated using an Android™ based hardware platform. In a non-limiting example, the evaluation application 188 which is an Android 4.4 or greater mobile device software designed to receive and display feeding data streamed from the housing assembly 150 during use. The evaluation application 188 is configured to execute multiple functions including provisioning of only authorized mobile devices 159, providing for secure user login to the evaluation application 188, inputting, manually or by bar code scanning, a subject identifier unique to the subject, providing for secure lookup and view of past feeding data for a subject, receiving feeding parameter input such as pacifier or nipple type, bottle type, fluid type, fluid volume, etc. collecting and displaying feeding data in real-time, using, for example and as shown in FIG. 16, the user interface 175 of the mobile device 159, and receiving user input and notations related to the subject and/or feeding session.

Figure 16:
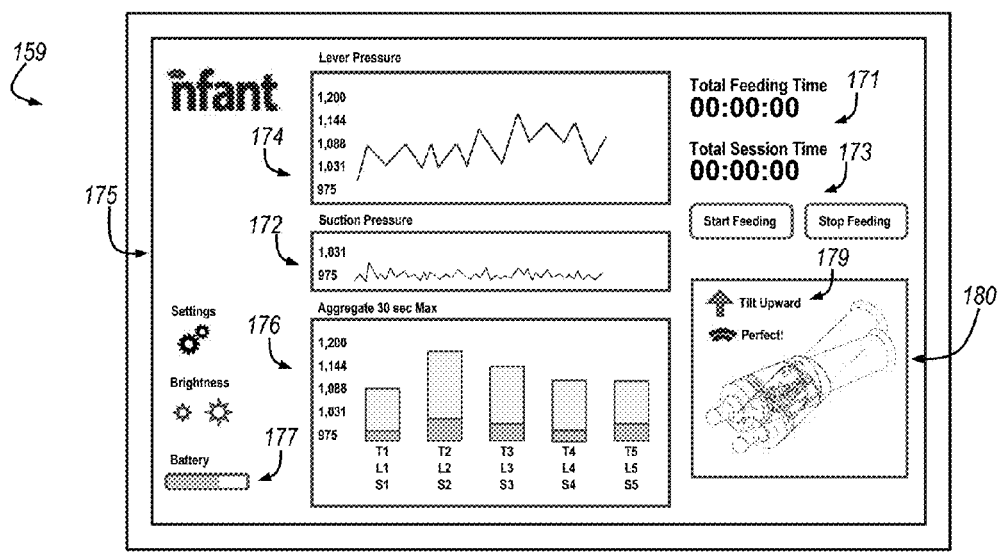
FIG. 16 is a schematic illustration of an exemplary display generated by the mobile device of FIG. 15.

By way of non-limiting example, an example of data which may be displayed by user interface 175 of the mobile device 159 is shown in FIG. 16. It would be understood that the example shown in FIG. 16 is one of a plurality of data screens which may be displayed to and/or manipulated by a user. User manipulation of the data screens may include, for example, selecting a data screen configuration from a menu of available data screens, viewing and/or zooming in or out of sub-screens such as a lever pressure screen 174 displaying output from the second sensor 79B corresponding to pivoting of the intermediate device 37, e.g., the lever, by the nipple element 11 and in response to the applied tongue force FT of the subject, or such as a suction pressure screen 172 displaying output from the first sensor 79A corresponding to the change in fluid pressure of the fluid in the fluid passage 97 of the coupling device 90, selecting and/or viewing aggregate pressure display 176, etc. User manipulation of the data screens may include, for example, starting and stopping feeding timers 171 using controls 173, viewing bottle tilt orientation 180 determined by output from the accelerometer 134 and adjusting the bottle position relative to the subject as indicated by a tilt alert display 179, monitoring a battery power indicator 177 for indications of a need to change the battery 77 on the unit, accessing the settings for selection of other screens or to perform administrative functions such as identifying the subject and/or the housing assembly 150 to the evaluation application 188, adjusting the screen brightness for viewability or environmental conditions such as night time feedings, etc. The user display 175 may be configured as a touch screen and include an onscreen touch keyboard, such that manipulation and input to the user display 175 and the evaluation application 188 can occur with the need for an external keyboard, mouse, etc., for the convenience of the user in manipulating the user display 175 while holding an infant subject and/or the evaluation apparatus 100E during an evaluation feeding session. In another example, an external keyboard and/or mouse, which may be wireless, may be operatively connected to the mobile device 159 and used for data input and display manipulation.

The mobile device 159 is in communication with a web portal 160 either directly or through a network 170, via the device communication interface 135 and a network interface 161 of the web portal 160. The network 170 may also be known as the Internet. The web portal 160 includes the network interface 161, an administrator interface 164 configured to display information including data, analysis results, messages, etc. to an administrator, a CPU/processor 162 and a memory 163. Each of the network interface 161, the administrator interface 164, and the CPU/processor 162 may include and/or be in operative communication with the memory 163, which may be configured as one or more of Read Only Memory (ROM), Random Access Memory (RAM), electrically-erasable programmable read only memory (EEPROM), etc., of a size and speed sufficient for executing the functions performed by the respective network interface 161, the administrator interface 164, and the CPU/processor 162, to store and execute applications used in administering the functions of the evaluation system 105A. Administrative functions performed by the web portal 160 may include, for example, storing and aggregating subject data in one or more databases, analyzing and reporting subject data for clinician interpretation, administrating protocols for data encryption of data communicated, displayed and/or otherwise transferred between the mobile device 135, the evaluation apparatus 100E and/or the web portal 160, authenticating users of the evaluation system 105A and the data generated by the evaluation system 105A, administering of protocols to protect and encrypt data for cloud storage of data and/or compliance with Health Insurance Portability and Accountability Act (HIPPA) privacy rules in the United States and similar regulations in other regions or countries, and/or otherwise securing the transfer of data using data encryption protocol such as Secure Hypertext Transfer Protocol (HTTPS), Secure Socket Layer (SSL) and administering related code keys which may include public/private key pairs for securing the web portal 160. The web portal 160 administers a database which includes unique identifiers assigned to each of the housing assemblies 150, time-sensitive provisioning codes used for temporary security identity during initial launch of the evaluation application 188 on a new mobile device 159, login keys identifying the mobile application 188 and each housing assembly 150 to the web portal 160, and pairs a unique subject identifier with each unique housing assembly 150.

Figure 17:
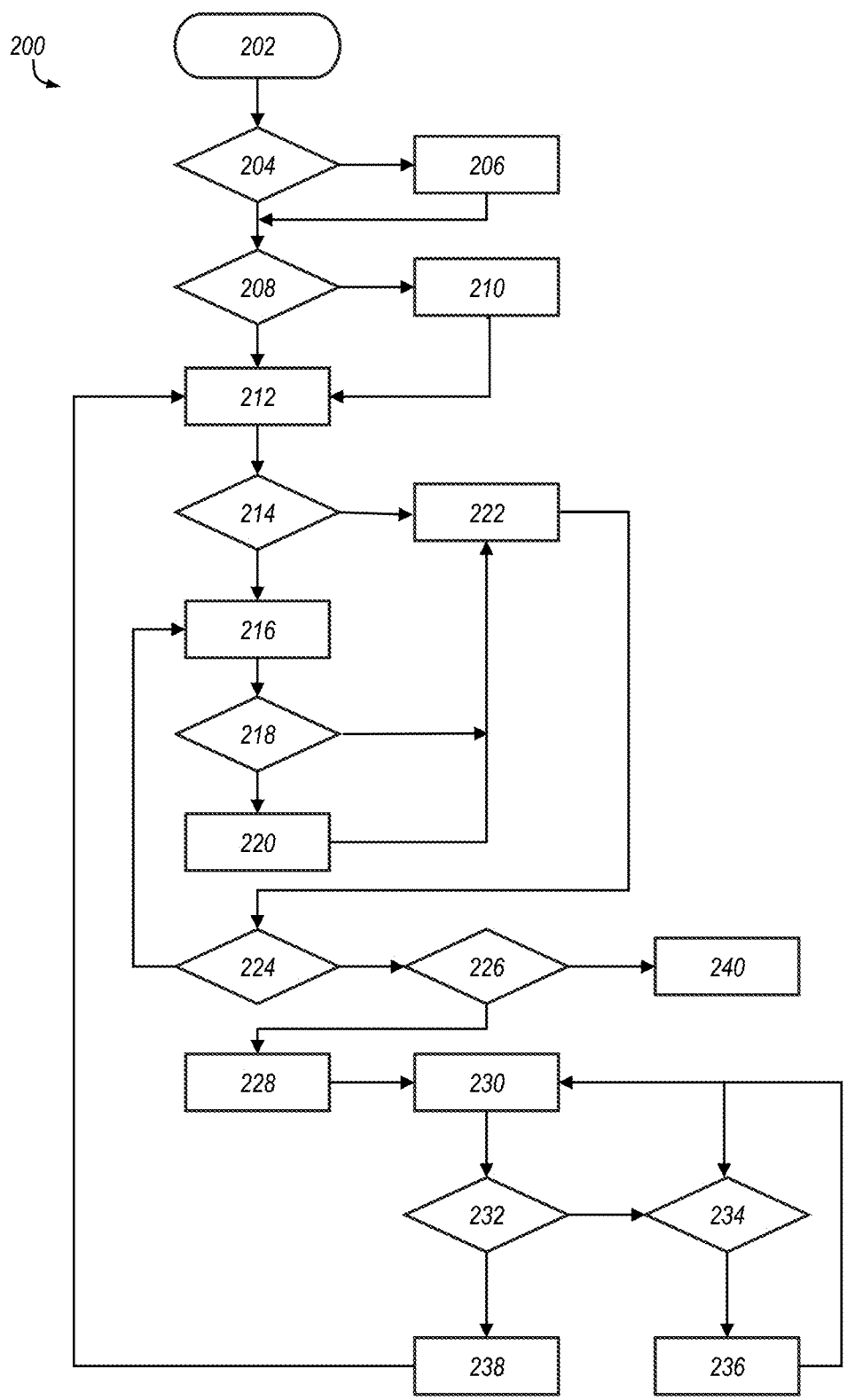
FIG. 17 is a schematic flow diagram of a process for evaluating the tongue movement and/or tongue strength of a subject using the system of FIG. 15.

Referring to FIG. 17, shown is an exemplary method 200 for use by a user to access and utilize the evaluation system 105A, including the evaluation apparatus 100E, to evaluate the tongue movement and tongue strength and coordination of a subject. At step 202, the user launches the evaluation application 188 on a mobile device 159. At step 204, a determination is made by the evaluation application 188 and/or the web portal 160 in communication with the evaluation application 188, of whether the mobile device 159 has been provisioned. If the evaluation application 188 has not yet been provisioned to the mobile device 159, the user obtains a provisioning code from the web portal 160, which associates the user with the mobile device 159, and/or with mobile devices 159 in an administrative unit to which the user is authorized. At step 206, the user enters the provisioning code to the evaluation application via the mobile device 159, which identifies the provisioned evaluation application 188 as being associated with the mobile device 159, thereby provisioning the evaluation application 188 and associated mobile device 159. On subsequent launches of the provisioned evaluation application 188 on the provisioned mobile device 159, the method will proceed directly from step 202 to step 208, with the web portal 160 recognizing the evaluation application 188 and the associated mobile device 159 as a single entity.

At step 208, the evaluation application 188 determines if the user has been authenticated. If the user has already been authenticated, for example, has already logged into the evaluation application 188, the method proceeds to step 212. If the user has not been authenticated, the method proceeds to step 210 and a login ID and passcode is requested by the evaluation application 188. The login ID and passcode credentials are provided to the user by an administrator, for example, from the web portal 160. After authentication of the user, the method proceeds to step 212, where the user selects the subject from a list displayed to the user by the evaluation application 188, a menu, by inputting the subject's identification information or otherwise. The evaluation application 188 at step 214 determined whether the subject is a new subject, e.g., has not been previously inputted to the system 105A. If the subject has already been entered into the system 105A, the method proceeds to step 222. Otherwise, the method proceeds to step 216, and the user enters the subject's data into the evaluation application 188, where the subject's data may include, for example, a subject identifier, which may be the subject's name, a patient number, or the like, the subject's age, weight, or other characteristics of the subject. At step 218, it is determined whether the housing assembly 150 including a sensing device 30 has already been paired to the new subject. If so, the method continues to step 222. Otherwise, the method continues to step 220, and the user pairs a new, e.g., previously unused housing assembly 150 including a previously unused sensing device 30 to the patient. The pairing process includes the housing assembly 150, and more specifically, the communication module 132 of the housing assembly 150 being assigned to the subject, pairing with the evaluation application 188 using a unique identifier which is programmed into the communication module 132, e.g., in the present example, the Bluetooth® low energy (BLE) module 132, to establish communications between the housing assembly 150 and the evaluation 188, including enabling the streaming of data identifiable to the assigned subject from the housing assembly 150 to the evaluation application 188 during an evaluation session. If an individual housing assembly 150 is attempted to be assigned to more than one subject, the user is prompted and not authorized to continue until a new (previously unassigned) housing assembly 150 is presented for pairing.

At step 222, subject history, for established subjects, is displayed, which may include a feeding history, data history, etc. Actions for the evaluation session being conducted may also be displayed, including whether the evaluation session is to be performed as a nutritive (NS) or non-nutritive (NNS) session, if nutritive, the type and quantity of fluid to be provided, the length of time feeding data should be collected, etc., the type of nipple element 11 to be used, the type of coupling assembly 190 to be used, for example, if the compliance of the second membrane 126B is being specified for the session, etc. At step 224, the user is prompted to edit the subject's information, which may include, for example, updating the subject's weight or updating other health or general characteristics of the subject.

At step 226, the user begins feeding the subject, where the term feeding is non-limiting and can refer to a nutritive or non-nutritive evaluation session as directed by the instructions provided at step 222. In a nutritive feeding evaluation session, the user assembles the evaluation apparatus 100E including a nipple element 11 having an aperture 25 through which the subject can ingest nutritive fluid which the user provides to the container 40 in sufficient quantity to ensure the sensor plug 120 remains fully immersed in fluid for the duration of the feeding session, before attaching the container 40 to the coupling device 90. In a non-nutritive feeding evaluation session, the user assembles the evaluation apparatus 100E including a nipple element 11 which may be a pacifier or other non-nutritive nipple type, and provides a fluid to the container 40 in sufficient quantity to ensure the sensor plug 120 remains fully immersed in fluid for the duration of the feeding session, before attaching the container 40 to the coupling device 90. When the feeding session is completed, the method continues to step 240 and the subject's history, which may include additional data from the current feeding evaluation session, is reviewed. At step 240, the user may logout from the evaluation application 188 and the system 105A, indicating the end of the feeding session. The subject's data and file history including data transmitted during the current feeding evaluation session from the assigned housing assembly 150 to the evaluation application 188 and stored, for example, on the memory 178 of the mobile device 159 may be transmitted to the web portal 160 via the network 170 for storage, analyzing, review by a clinician/administrator for recommendation of a subsequent action plan, etc. when a network connection to the network 170 is next established by the mobile device 159. An active connection between the mobile device 159 and network 170 is not needed to perform data collection during a feeding evaluation session.

At the beginning of feeding at step 226, the evaluation application 188 at step 228 gathers pre-information from the housing assembly 150 which may include, for example, the battery voltage, accelerometer orientation, etc. The pre-information may include, for example, scanning an identifier bar code of the housing assembly 150 and/or entering it manually to the evaluation application 188 to ensure the housing assembly 150 being used for the feeding session is assigned to the subject being fed. At step 230, the evaluation application 188 receives feeding data from the sensing device 30 in the housing assembly 150, which is transmitted wireless via the communications module 132 to the evaluation application 188. The feeding data includes, for example, a series of number values representing pressure sensor readings from each of the first and second pressure sensors 79A, 79B, which may be displayed as shown, respectively, in data displays 172, 174 on the user interface 175 of the mobile device 159.

At optional step 232, the feeding may be paused, for example, to add fluid to the evaluation apparatus 100E, to burp the infant subject, etc. The user may provide an input to the evaluation application 188, to indicate the feeding is paused and the evaluation session is not yet completed. While feeding is paused, for example, at step 234, the nipple element 11 may be changed, to provide a nipple element 11 of a different type and/or having a different compliance thereby changing the resistive force exerted by the nipple element 11 against the tongue of the subject. The nipple element 11 may be changed to another nipple element 11 to change the compliance, for example, if required to decrease the compliance for a subject with relatively less tongue strength and coordination, to enable continued feeding. In another example, the nipple element 11 may be changed to another nipple element 11 to increase the compliance, thereby increasing the resistive force FR exerted against the tongue of the subject, for therapeutic reasons, for example, to exercise and/or strengthen the tongue. If the nipple is changed at step 234, the method proceeds to step 236 where the change in nipple element 11 is recorded, and feeding at step 230 is recommenced. When feeding is paused at step 232 to terminate the feeding evaluation session, the method proceeds to step 238, where post session metrics are gathered by the evaluation application 188 and/or input to the evaluation application 188 by the user. Post session metrics may include, for example, the battery charge remaining at the end of the session, the amount of fluid consumed by the subject during the session, notes and/or observations made of the subject's condition, etc. The session for that subject then terminates, and the evaluation application may, for example, return to display the patient selection menu at step 212 in preparation for a subsequent session.

An intervention method is described in U.S. non-provisional application Ser. No. 13/479,640 filed May 24, 2012 and issued as U.S. Pat. No. 8,663,131, incorporated herein in its entirety. In the intervention method, the compliance of the nipple element 11, and/or the compliance of a compliance element 80 having a known compliance may be used to evaluate and/or to therapeutically develop a subject's tongue strength and coordination. As previously described herein and applied to the intervention method described in U.S. Pat. No. 8,663,131, sensor plugs 120 having a second membrane 126B of known compliance can be used therapeutically with the evaluation apparatus 100E, where various coupling assemblies 190 having sensor plugs 120 of different, e.g., graduated, compliance, and could be used in a sequence to gradually increase the resistance force FR exerted by the lever end 69 on the tongue facing portion 21 of the nipple element 11, by increasing the resistive membrane force FM component of the effective resistance force FR, for the purpose of exercising the subject's tongue and increasing the tongue strength and coordination and deformation force FT exerted by the tongue of the subject.

The examples provided herein are non-limiting, and it would be understood that other configurations of the sensing apparatus 130, sensing device 30, sensor plug 120, intermediate device 37, coupling device 90, etc. could be used to provide the functions and execute the methods described herein. It would be understood that the housing 140 or portions thereof such as the bridge portion 181, sensing apparatus 130 including the sensing device 30 and the sensor plug 120, the intermediate device 37, and/or the coupling element 93 or portions thereof such as the central portion 193, individually and/or in combination of one or more of these elements could be used for sensing of various parameters including, by way of non-limiting example, mechanical force, pressure, etc., in applications other than those disclosed by the figures. For example, it would be understood that the housing 140, the sensing apparatus 130 including the sensing device 30, and the sensor plug 120, may be arranged and/or configured such the sensing device 30 is positionable relative to the sensor plug 120 to sense movement of at least one membrane 126 defined by the sensor plug 120 by an input causing movement of the at least one membrane 126, such as a mechanical input or a pressure input, to correlate movement of the at least one membrane 126 to the input.

By way of non-limiting example, the sensing apparatus 130 including the sensing device 30 and plug insert 120 could be configured with one, two, three or more sets of sensors 79, sensor ports 107 and membranes 126, to concurrently measure one, two, three or more parameters. The sensor apparatus 130 may include at least two sets of sensors 79, sensor ports 107 and membranes 126 configured to measure the same parameter, for example, fluid pressure changes in the fluid passage 97, for comparison of the sensor outputs and/or to provide an output as an averaged value of the at least two sets. The sensing apparatus 130 including the sensor plug 120 and sensing device 30 may be used with a sensor housing defining at least one port 107 in applications other than the coupling device 90 described herein. Other configurations and/or shapes of actuators 74 may be used, multiple actuators 74 may be used, and the actuator(s) 74 may be positioned in locations on the lever, other than that illustrated in the figures. For example, an actuator 74 may be located on the tail 67, or positioned on the lever bar 68 closer to the lever end 69. The coupling device 90 may be configured to include multiple sensing devices interfacing with multiple sensor plugs connected to the coupling device 90.

The detailed description and the drawings or figures are supportive and descriptive of the invention, but the scope of the invention is defined solely by the claims. While some of the best modes and other embodiments for carrying out the claimed invention have been described in detail, various alternative designs and embodiments exist for practicing the invention defined in the appended claims.

The invention claimed is:

1. A device comprising:
a wall defining a passage;
the wall defining an aperture in communication with the passage;
a sensor plug enclosing and sealing the aperture;
a receiver disposed in the passage;
a lever defining a lever end, a tail end, and a pivot point intermediate the lever end and the tail end;
wherein the lever is pivotably attached to the receiver at the pivot point;
wherein deflection of the lever end causes an actuator defined by the lever to actuate movement of the sensor plug;
a housing attachable to the wall;
the housing encompassing a port;
wherein a sensor is disposed in the port; and
wherein, with the housing attached to the wall, the port is in contact with the sensor plug and the sensor is in communication with the sensor plug via the port.

2. The device of claim 1, wherein the actuator is in contact with the sensor plug.

3. The device of claim 1, wherein
the sensor is configured to sense movement of the sensor plug;
wherein the sensor plug is intermediate the sensor and the passage; and
wherein the sensor is configured to generate a sensor output corresponding to the movement of the sensor plug.

4. The device of claim 3, wherein the sensor output is correlated to the deflection of the lever end.

5. The device of claim 1, further comprising:
a membrane defined by the sensor plug;
wherein the actuator is in contact with the membrane such that deflection of the lever end causes movement of the membrane.

6. The device of claim 1, wherein the actuator is in continuous contact with the membrane such that the membrane exerts a membrane force on the actuator in opposition to an actuation force exerted by the actuator on the membrane.

7. The device of claim 6, further comprising:
a passage opening in communication with the passage and defined by the wall;
wherein the lever end extends out of the passage via the passage opening.

8. The device of claim 7, further comprising:
a coupling element comprising a coupling end and the wall;
wherein the coupling end is configured to receive a nipple element such that the passage is in fluid communication via the passage opening with a nipple cavity defined by the nipple element.

9. The device of claim 8, wherein the lever end extends into the nipple cavity such that the lever end is detached from and in contact with a nipple surface defining the nipple cavity.

10. The device of claim 9, wherein the lever end is deflectable by deformation of the nipple element to pivot the actuator relative to the membrane by a pivot angle.

11. The device of claim 10, wherein the deformation of the nipple element exerts a deformation force on the lever end via the nipple element;
wherein the actuation force exerted by the actuator pivoted by the pivot angle corresponds to the deformation force.

12. The device of claim 10, where the membrane exerts the membrane force in resistance to the deformation force.

13. The device of claim 1, wherein:
- the port, the sensor and the membrane define a sealed chamber;
- the sensor is a pressure sensor in communication with the sealed chamber to sense a change in a chamber pressure of the sealed chamber; and
- the change in chamber pressure corresponds to the movement of the membrane by the actuator.

14. The device of claim 1, wherein the housing is removably attachable to the wall.

15. The device of claim 1, wherein the receiver is integral to the wall.

16. The device of claim 1, further comprising:
- a fulcrum defined by the receiver;
- the fulcrum defining the pivot point; and
- wherein the lever defines a pivot element which is pivotably attached to the fulcrum at the pivot point.

17. The device of claim 1, wherein the actuator is intermediate the lever end and the tail end.

18. The device of claim 1, wherein the actuator is intermediate the pivot point and the lever end.

* * * * *